United States Patent
Fält et al.

(10) Patent No.: US 10,446,262 B2
(45) Date of Patent: Oct. 15, 2019

(54) SYSTEMS AND METHODS FOR SIMULATION-BASED RADIATION ESTIMATION AND PROTECTION FOR MEDICAL PROCEDURES

(71) Applicant: Mentice Inc., Evanston, IL (US)

(72) Inventors: Edvard Per Gösta Fält, Gothenburg (SE); Lars Birger Lönn, Copenhagen (DK)

(73) Assignee: MENTICE INC., Evanston, IL (US)

( * ) Notice: Subject to any disclaimer, the term of this patent is extended or adjusted under 35 U.S.C. 154(b) by 621 days.

(21) Appl. No.: 15/072,142

(22) Filed: Mar. 16, 2016

(65) Prior Publication Data
US 2016/0196406 A1 Jul. 7, 2016

Related U.S. Application Data

(63) Continuation of application No. 14/509,001, filed on Oct. 7, 2014, now Pat. No. 9,323,896.

(60) Provisional application No. 61/887,835, filed on Oct. 7, 2013.

(51) Int. Cl.
*G01N 33/48* (2006.01)
*G01N 33/50* (2006.01)
(Continued)

(52) U.S. Cl.
CPC ............... *G16B 50/00* (2019.02); *A61B 6/10* (2013.01); *A61N 5/1075* (2013.01);
(Continued)

(58) Field of Classification Search
None
See application file for complete search history.

(56) References Cited

U.S. PATENT DOCUMENTS 7,792,249 B2 * 9/2010 Gertner ................. A61F 9/008
378/65
9,323,896 B2 * 4/2016 Falt ....................... A61N 5/1075
(Continued)

FOREIGN PATENT DOCUMENTS

| GB | 2484355 | 4/2012 |
| JP | 2012-055510 | 3/2012 |
| WO | 2011/048515 | 4/2011 |

OTHER PUBLICATIONS

Muniyandi et al. Real-time Pc based X-ray simulation for interventional radiology training. Medicine Meets Virtual Reality, vol. 11, pp. 233-239. (Year: 2003).*

(Continued)

*Primary Examiner* — Russell S Negin
(74) *Attorney, Agent, or Firm* — Bryan Cave Leighton Paisner LLP

(57) ABSTRACT

Systems and methods for determining radiation exposure during an x-ray guided medical procedure are disclosed. In some embodiments, the system includes an x-ray equipment model that simulates the emission of radiation from x-ray equipment during the x-ray guided medical procedure, a human exposure model that simulates one or more human anatomies during the x-ray guided medical procedure, a radiation metric processor that calculates at least one radiation exposure metric, and a feedback system for outputting information based on the at least one radiation exposure metric. The radiation metric processor calculates radiation exposure metrics based on input parameters that correspond to operating settings as well as the location and structure of one or more human anatomies.

20 Claims, 19 Drawing Sheets

(51) Int. Cl.

| | |
|---|---|
| *G16B 50/00* | (2019.01) |
| *A61N 5/10* | (2006.01) |
| *G16B 5/00* | (2019.01) |
| *G16B 45/00* | (2019.01) |
| *A61B 6/10* | (2006.01) |
| *G09B 23/28* | (2006.01) |
| *G16H 40/63* | (2018.01) |
| *G16H 50/50* | (2018.01) |

(52) U.S. Cl.
CPC ............. *G09B 23/286* (2013.01); *G16B 5/00* (2019.02); *G16B 45/00* (2019.02); *G16H 40/63* (2018.01); *G16H 50/50* (2018.01); *A61B 6/107* (2013.01); *A61N 2005/1094* (2013.01)

(56) References Cited

U.S. PATENT DOCUMENTS

| | | |
|---|---|---|
| 2012/0148131 A1 | 6/2012 | Couch et al. |
| 2012/0314842 A1 | 12/2012 | Kargar et al. |
| 2013/0051527 A1 | 2/2013 | Sakaguchi et al. |

OTHER PUBLICATIONS

Notice of Reasons for Rejection, Japanese Application No. 2016-521620, dated Mar. 21, 2017.
Extended European Search Report, European Application No. 14851932, dated Aug. 2, 2017.

\* cited by examiner

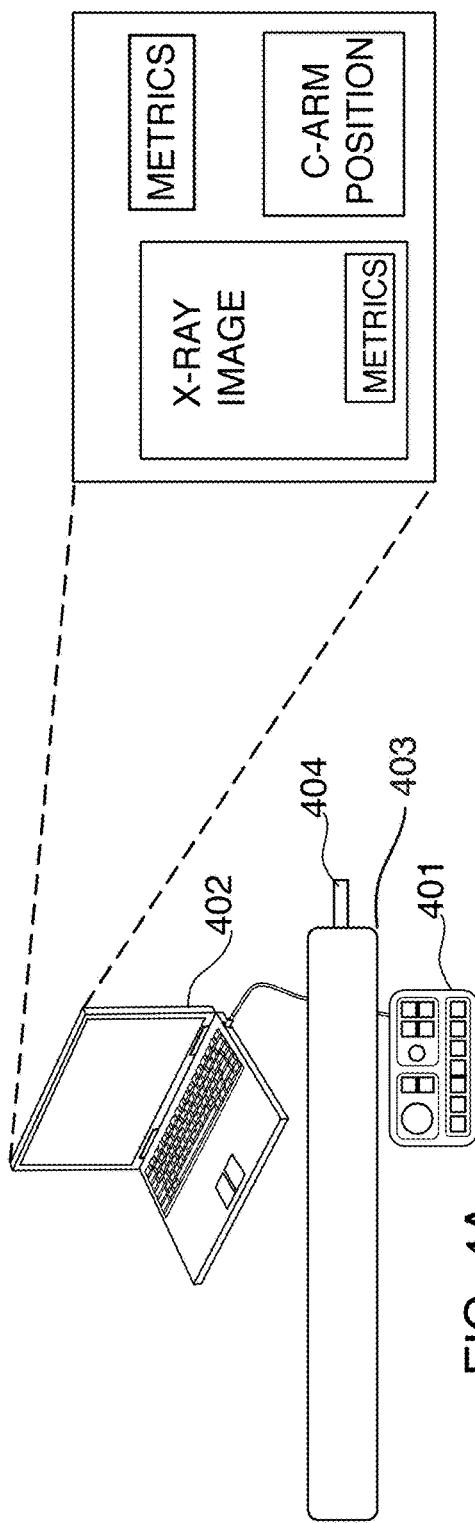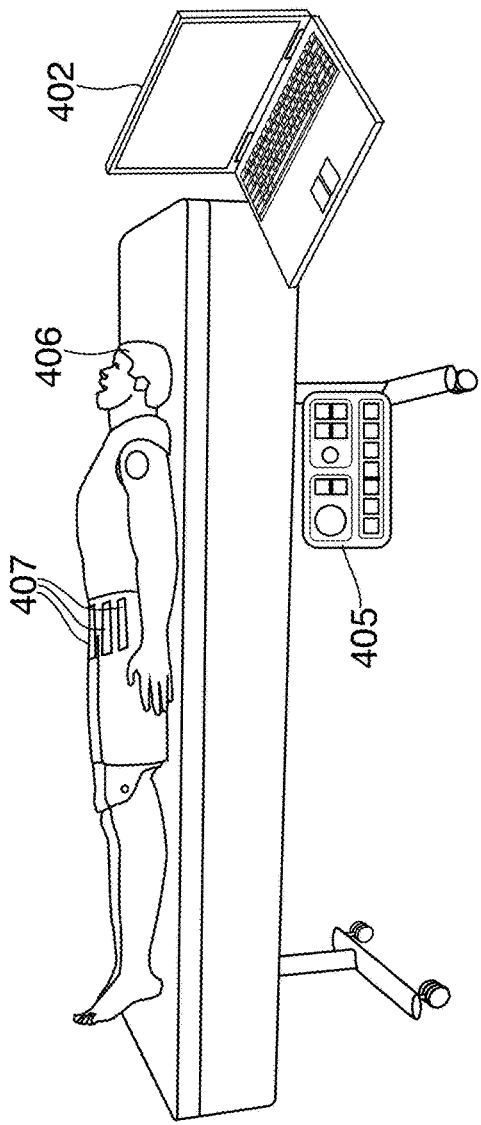
FIG. 4A
FIG. 4B

High x-ray noise, low contrast

Low x-ray noise, high contrast

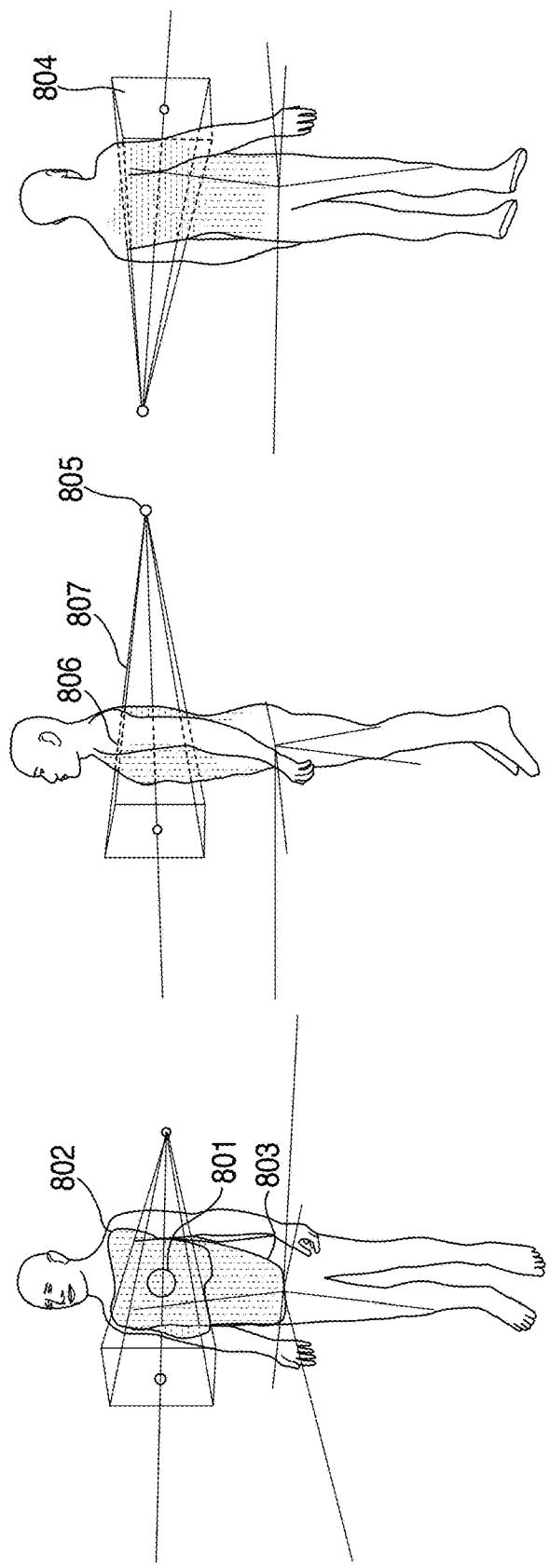

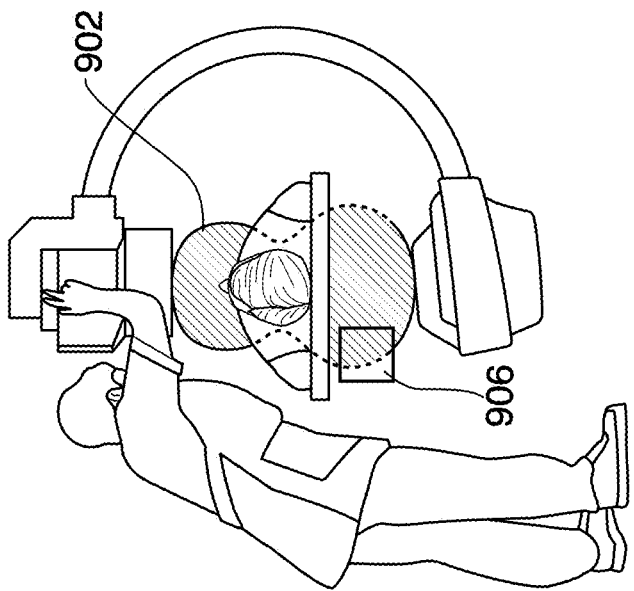
FIG. 9B Head view
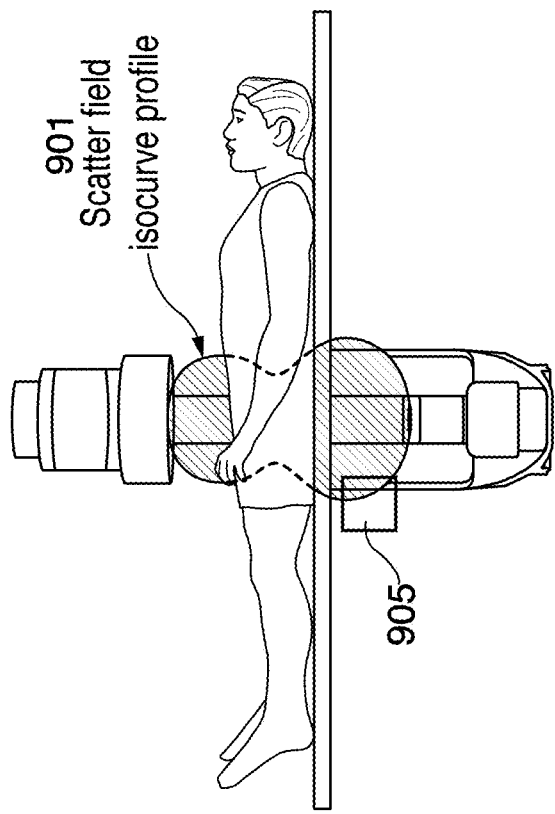
FIG. 9A Side view

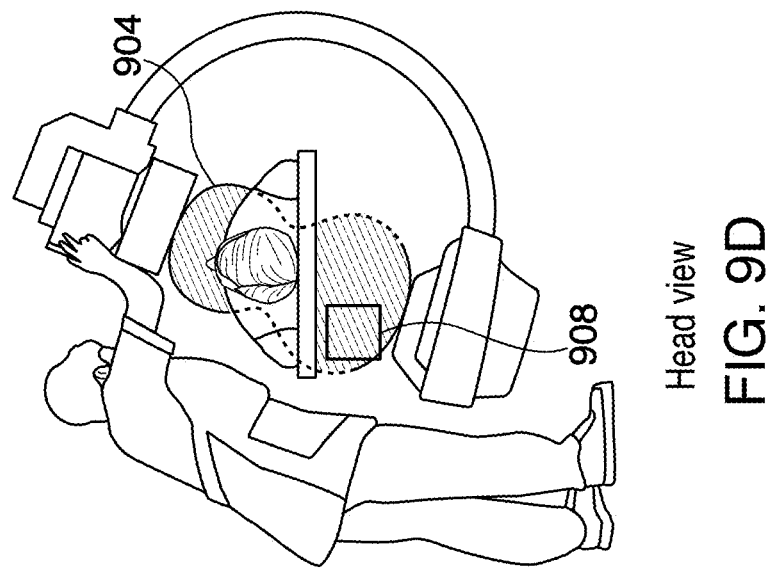
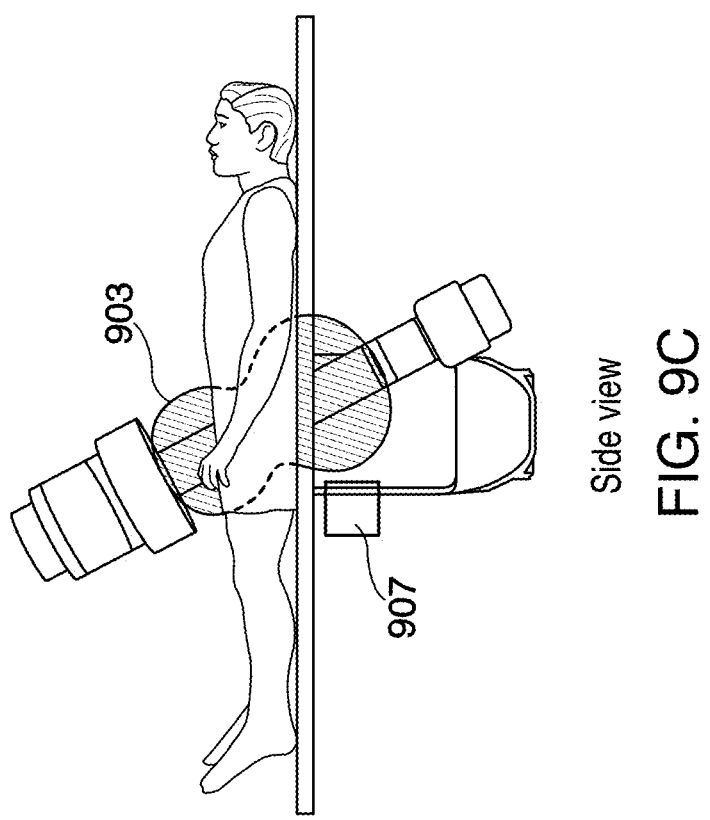
Side view
FIG. 9C
Head view
FIG. 9D

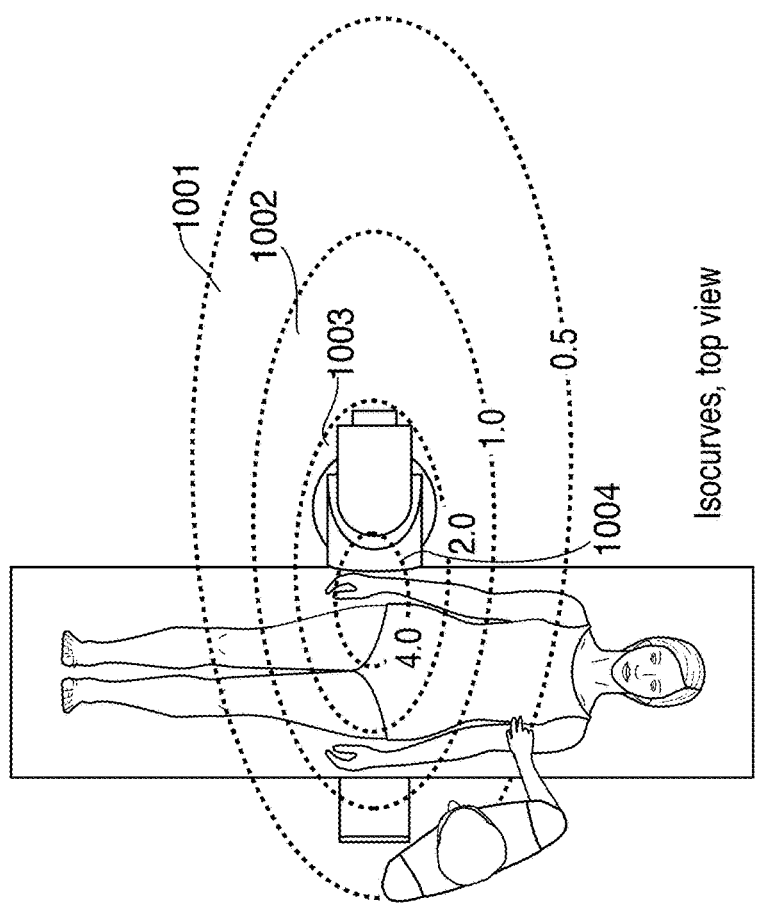
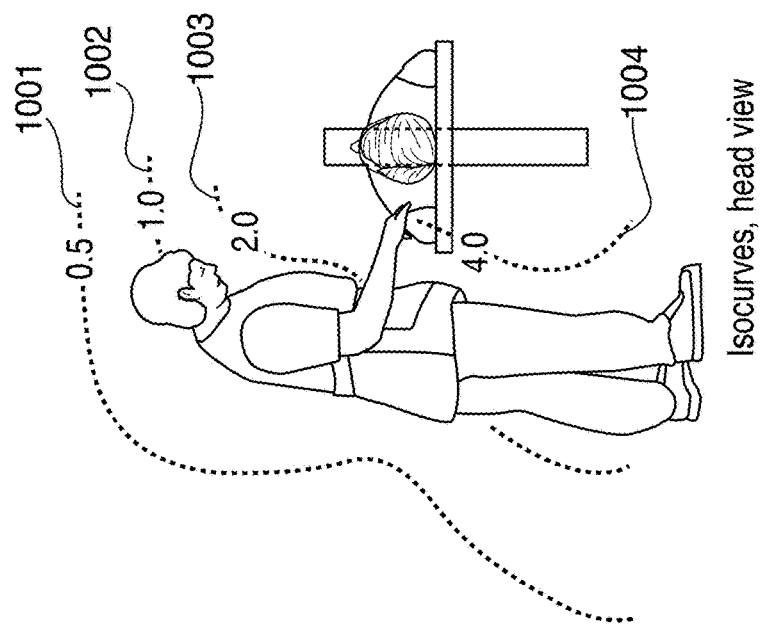
FIG. 10B
FIG. 10A

RDSR container

Irradiation Event Type : Fluoroscopy
Irradiation Event Type : Fluoroscopy
Irradiation Event Type : Fluoroscopy
DateTime Started :
Dose Area Product = 0.002 Gym2
Dose (RP) = 0.02 Gy
Position Primary Angle = 36.20 °
Position Secondary Angle = -62.30°
Collimated Field Area = 0.1 m2
Pulse Rate = 15 pulse/s
Irradiation Duration = 52 s
Distance Source to Detector = 100 mm
Table Longitudinal Position = 10mm
Table Lateral Position = 10mm
Table Height Position = 10mm

FIG. 14B

SYSTEMS AND METHODS FOR SIMULATION-BASED RADIATION ESTIMATION AND PROTECTION FOR MEDICAL PROCEDURES

CROSS-REFERENCE TO RELATED APPLICATIONS

The present application is a continuation application of U.S. application Ser. No. 14/509,001 filed on Oct. 7, 2015, which claims priority to U.S. Provisional Patent Application No. 61/887,835 filed on Oct. 7, 2013, which is incorporated herein by reference in its entirety.

FIELD OF THE INVENTION

The invention is related to systems and methods for simulating radiation exposure to patients or medical teams during an image-guided medical procedure, and in particular to simulating the radiation exposure of an x-ray based image-guided procedure, such as fluoroscopy.

BACKGROUND OF THE INVENTION

Medical equipment that uses ionizing radiation has found widespread application in the healthcare industry today. Allowing medical teams to diagnose and treat patients effectively, ionizing radiation has been used in different branches of medicine including, radiology, cardiology, neurology, oncology, trauma care, orthopedic surgery, endovascular intervention. The benefits of using x-ray imaging as a diagnostic tool and as a treatment option continue to grow. Non-communicable diseases (NCDs), which include cardiovascular diseases, cancer, diabetes and chronic respiratory diseases, have benefited greatly from the use of x-ray imaging. According to the World Health Organization, the global epidemic of NCDs is now the leading cause of death in the world.

The types of equipment that are typically used in these fields and responsible for the emission of ionizing radiation include CT scanners, fluoroscopes, and radiology x-ray cameras. Ionizing radiation is also prevalent in nuclear medicine and molecular imaging processes, where radioactive substances are introduced into a patient's body.

However, exposure to radiation typically results in serious side effects, including microscopic damage to living tissue. Tissue damage can sometimes cause skin burn or radiation sickness (also commonly referred to as "tissue effects", or "deterministic effects"), and in some cases, cancer ("stochastic effects"). This type of tissue damage is a risk to both the patient, as well as the medical teams that work in these environments, because of secondary "scatter" radiation. Secondary scatter radiation is harmful radiation that the medical team is exposed to as a result of scattering off of a patient or other objects in the environment.

As a way of managing this tradeoff between potential benefit and potential harm from using x-ray, the concept of ALARA (As Low As Reasonably Achievable) has been introduced. ALARA is a radiation safety principle based on the assumption that every radiation dose of any magnitude can produce some level of detrimental effects, and ALARA is therefore aimed at minimizing radiation doses by employing all reasonable methods. In most parts of the world, ALARA is also a regulatory requirement.

The rate of medical radiation exposure has grown rapidly over the past several decades. Recent studies suggest that over half of the total radiation exposure to the general public comes from medical radiation. Studies further suggest that the exposure of the US population to ionizing radiation from diagnostic medical procedures had grown by more than seven times from the early 1980s. Procedures that contributed to this growth the most include CT-based procedures, nuclear medicine-based procedures, and interventional fluoroscopy.

Several recent trends show that fluoroscopic procedures will soon outpace CT-based procedures and become one of the types of procedures with the highest association to radiation exposure. For one, fluoroscopy guided procedures have become increasingly popular as they are commonly used to treat NCDs. Moreover, medical teams have been transitioning to minimally invasive x-ray guided surgery in favor of open surgery, especially with the rapid development of new endovascular techniques. Fluoroscopic procedures are expected to pose a higher risk of radiation exposure in comparison to CT-based procedures, in part due to recent advancements that have lowered the exposure in CT-based procedures. For example, improvements in CT scanning technology have made it possible to run CT scans using only a fraction of the radiation that was previously required. In contrast, radiation exposure metrics remain high for other x-ray guided procedures, such as interventional fluoroscopic procedures. Further, legislation and guidelines have recently been passed that limit the utilization of CT scans.

Compared to CT-based procedures, medical teams can change the operating settings of the x-ray equipment during the course of the fluoroscopic procedure. These operation settings are changed dynamically during the fluoroscopic procedure and affect the amount of radiation delivered to the patient and medical team, as well as the image quality produced by the equipment. Since the team is performing an operation on the patient during interventional fluoroscopy, it is not possible for them to reduce their own exposure by maintaining a large distance to the x-ray source while imaging, such as is the practice for diagnostic CT scans. There are a number of different input parameters that correspond to operating settings that may impact the level of radiation exposure delivered to the patient or the medical team, and these parameters may be interrelated or functionally dependent. For example, the radiation dose rate may be impacted by the path length that the central beam travels through the body, the patient's thickness, table and c-arm movement and angulation, the part of the body being imaged, the fluoroscopic pulse rate of the x-ray machine, fluoroscopic dose level (low/normal/high), cine acquisition (on/off), cine acquisition frame rate, C-arm detector height, collimation (square or round), the number of wedge filters being used, the magnification or Field of View (FOV), the use of Digital Subtraction Angiography (DSA), the changing of a patient's position (habitus) on the table, the dose protocols being used for specific procedures, x-ray tube voltages and currents, the use of beam shaping filters, the use of automatic dose rate control (ADRC), the location of the radiation source (above or below the patient table), or the use of an image intensifier instead of flat panel. A change to a single parameter or combination of parameters may change the radiation dose rate to the patient or medical team. However, it is very difficult for a medical professional to develop a good understanding of the harmful effects of such changes, since radiation is neither visible nor otherwise noticeable to humans. Further, changes to a single parameter or combination of parameters may change the quality of the x-ray image produced by the x-ray machine, something which may influence correct decision making in the delivery of treatment. Because these parameters may be interrelated or functionally dependent, accurately determining how a change to a parameter affects radiation dose rate or image quality is computationally complex. Yet, understanding the complex relationship between equipment settings, image quality and resulting exposure allows medical teams to minimize health risks to patients and themselves while optimizing image and treatment quality.

Currently, medical teams do not receive training that shows how a change to an operation setting during a fluoroscopic procedure causes a change to the radiation exposed to the patient or medical team. Despite the need for a detailed understanding of radiation reduction techniques, most medical teams today only receive a review of the basic concepts of radiation exposure, without any hands-on training. Training modules typically do not include any hands-on components, because there is currently no effective way of providing realistic hands-on training without using real radiation. Although some training programs use empty operating rooms and "phantoms" as substitutes for patients, several drawbacks exist. Specifically, these training programs still expose medical teams to secondary radiation and they block the operating room from being used for real procedures. Furthermore, they do not show how changes to operating settings during an operation cause changes in radiation exposure and image quality, or how operating settings may need to be changed at different points of an x-ray guided medical procedure to balance the trade-off between radiation exposure and image quality.

Although techniques and systems for measuring, estimating, and visualizing radiation exposure have been developed, none of the presently known art describes a comprehensive solution for training medical professionals or teams on the effects of operating setting adjustments and their impact on radiation exposure and image quality in a highly realistic and completely radiation-free simulated environment. The closer the simulation emulates the real world, the higher the transfer-of-training effect into the real operating room will be.

Further, systems for measuring, estimating, and visualizing radiation exposure do not show how changes in a simulation parameter affect radiation dynamically during the course of a procedure. Simulations that take into account multiple different simulation parameters are often computationally complex, and generally executed in a time- and resource-intensive Monte Carlo-style fashion. Further, to change a set of parameters, the simulation is generally re-executed, and thus, unable to effectively show how changes to a parameter affect radiation during a live procedure.

Moreover, systems for measuring, estimating, and visualizing radiation exposure do not provide any meaningful information about the risk levels associated with different levels of radiation exposure. In comparison to radiation exposure, there are generally no direct indications of the degree of risk. Integrating an effective means of showing how to assess health risk and evaluate damage is therefore needed.

Accordingly, there is a need for a training system that allows medical students, physicians and hospital staff to exercise the skills needed to minimize exposure during x-ray guided procedures in a hands-on, radiation-free and highly realistic environment. Further, there is a need for a training system that makes it easy for them to develop a thorough understanding of how the resulting dose will be affected by using different procedural techniques.

SUMMARY OF THE INVENTION

Methods and systems for simulating an x-ray guided medical procedure on a human and calculating the radiation exposure to one or more humans during the x-ray guided medical procedure are disclosed. The methods and systems disclosed enable a user to determine a change in radiation metrics based on a corresponding change to an input parameter to an x-ray equipment model or human exposure model. By determining the change in radiation metrics, the methods and systems may output current and cumulative radiation metrics live, during the x-ray guided procedure. The updated metrics further enable the methods and systems to provide feedback and performance evaluations to the user. By providing information about the amount of radiation being exposed to the patient or medical team, the user may adjust the input parameters to achieve an optimized balance between radiation exposure, x-ray image quality, and risks associated with the exposure during the procedure. For example, during an endovascular procedure, the user may adjust the input parameters in response to radiation metrics indicating a dangerous level of exposure.

The system may include an x-ray equipment model and a human exposure model for providing system input, a radiation metric processor, and a feedback system. The x-ray equipment model simulates the emission of radiation from an x-ray machine during the x-ray guided procedure. The x-ray equipment model also enables a user to set and adjust input parameters. Input parameters correspond to operating settings controlled during the x-ray guided procedure. The input parameters are configured to be varied over the course of the x-ray guided procedure. The human exposure model simulates the structure of one or more human anatomies during the x-ray guided procedure.

The radiation metric processor calculates radiation exposure metrics to one or more humans located at the simulated x-ray guided medical procedure. The calculation of the radiation exposure metrics occurs during the x-ray guided medical procedure, and is based on the input parameters to the x-ray equipment and human exposure models. The radiation metrics are calculated with a model that associates a change in the input parameters with a change in the radiation exposure metric. In this way, when a user changes an input parameter, the methods and systems may output the change in radiation metrics during the procedure, without interruption.

The feedback system includes an x-ray imaging simulator and radiation metric display. The radiation metric display shows the first and second radiation exposure metrics to a user during the x-ray guided procedure. The x-ray imaging simulator generates an x-ray image of the human based on the x-ray equipment model and human exposure model at each point in time. The x-ray imaging simulator applies the noise pattern to the x-ray image to create a simulated noisy x-ray image. The x-ray imaging simulator then displays the noisy x-ray image to the user. In this way, the x-ray imagery shown to the user may be generated without using ionizing radiation; thus a user can train on a specific medical procedure in a realistic operating room environment, without exposing a patient, or him- or herself, or his or her team, to harmful radiation.

BRIEF DESCRIPTION OF THE FIGURES

The objects and features of the invention can be better understood with reference to the following detailed description and accompanying figures.

FIGS. 8A, B and C show an example of patient radiation dose heatmaps according to one embodiment of the invention.

FIGS. 9 A, B, C and D show scatter radiation according to one embodiment of the invention.

FIGS. 10A and B show cross-section visualizations of the scatter radiation isocurves according to one embodiment of the invention.

DETAILED DESCRIPTION OF THE INVENTION

The invention described herein provides systems and methods for the realistic simulation of x-ray guided medical procedures in a radiation-free environment. The system and methods may be used to train and certify professionals to reduce medical and occupational radiation exposure, and educate operators of x-ray systems how to use x-ray equipment in the least harmful way. Embodiments of the invention may also be used for therapeutic device design, development and testing.

Figure 1:
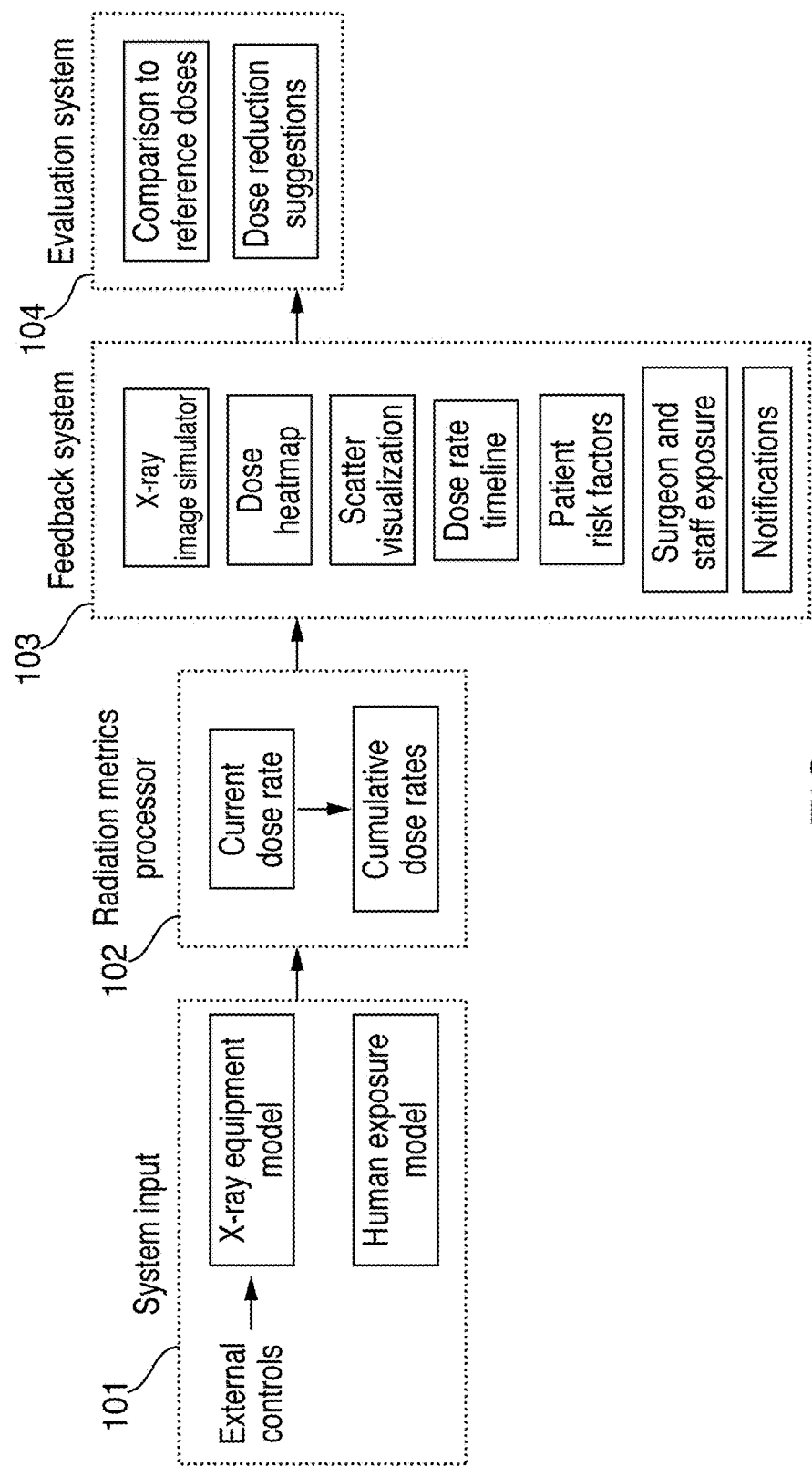
FIG. 1 is a block diagram for the several components of the system according to one embodiment of the invention.

FIG. 1 shows a diagram of several components of the radiation protection simulation system according to one embodiment of the invention. These components enable a user to simulate an x-ray guided procedure, and visualize the changes to radiation exposure and image quality as the user adjusts operating settings during the procedure. The components of the radiation protection simulation system may include a system input 101, radiation metrics processor 102, feedback system 103, and evaluation system 104. Using x-ray equipment and human anatomical information from system input 101, the radiation protection simulation generates radiation metrics, provides feedback, and evaluates the performance of a procedure. The radiation protection simulation components generate radiation metrics and feedback predictively, without exposing a user, patient, or individual on a medical team to ionizing radiation. Further, the radiation protection simulation components generate radiation metrics, feedback, and performance evaluation during the course of the procedure, providing a hands-on experience for the user that realistically simulates the changes in radiation exposure and x-ray image quality as settings are changed during the course of the procedure.

The x-ray equipment and human exposure models generate data that is input to the radiation metrics processor 102 which calculates radiation metrics, such as for example, dose rate and cumulative dose information. The radiation metrics processor may calculate radiation metrics for humans located in the room during the procedure, including the direct radiation exposure to the patient and scatter radiation to the medical team. During the course of an x-ray guided medical procedure, these radiation metrics may be provided to a feedback system 103 and displayed to a user. The feedback system 103 uses the radiation metrics to provide a realistic visualization of the x-ray imagery or scatter radiation generated by the x-ray equipment under current operating settings. By visualizing the radiation metrics, a user may adjust operating settings of the x-ray equipment to achieve a desired level of radiation dosage or x-ray image noise. An evaluation system 104 evaluates the user's performance and suggests strategies for improving his or her dose reduction techniques.

System input 101 allows a user to specify information about the x-ray equipment and location and structure of the anatomies of the patients or individuals of a medical team being used in the simulation. The simulation incorporates the information into x-ray equipment models and human exposure models that enable the simulation to determine how the equipment emits radiation and how the patient or medical team member is exposed to the radiation. The system input further enables users to change settings of x-ray equipment or patient/medical team member anatomy.

The x-ray equipment model may be selected to correspond to a common real-life configuration. For example, to configure the x-ray equipment model to correspond to a fluoroscopic x-ray equipment model, the user may select a flat panel detector, an x-ray source mounted under the table, and select automatic dose control capability. X-ray equipment models may be pre-installed on the radiation protection simulation system and presented to the user for selection, or the individual characteristics of the model may be configured at will by the user.

The human exposure models may consist of a library of models for the patient and/or the members of the operating team. For the patient, the model library may include a set of models representing various training objectives important for radiation protection training, for example different ages and weights, gender and pregnant patients. Such anatomy models may be obtained from CT or MRI data, or they may be modelled with three-dimensional modelling software, and may contain the skin of the patient as well as other organs. Alternatively, a pre-installed anatomy may be used, and the user may also be allowed to modify the appearance of the pre-installed model by entering anatomy parameters such as weight, length, or thickness. The human exposure models may correspond to anatomical features of the patient. In one embodiment, human exposure models may be anatomical measures such as length, height to the eyes, or height to the gonads. The user may modify these anatomical measures.

In one embodiment, the system input further includes x-ray equipment controls. The x-ray equipment controls emulate the controls that are typically used to control the operation of x-ray equipment. These controls may be, for example, the input parameters described above, such as table and c-arm movement and angulation, the fluoroscopic pulse rate of the x-ray machine, fluoroscopic dose level (low/ normal/high), cine acquisition (on/off), cine acquisition frame rate, C-arm detector height, collimation (square or round), the number of wedge filters being used, the magnification or Field of View (FOV), the use of Digital Subtraction Angiography (DSA), the dose protocols being used for specific procedures, x-ray tube voltages and currents, the use of beam shaping filters, the use of automatic dose rate control (ADRC), the location of the radiation source (above or below the patient table), or the use of an image intensifier instead of flat panel. Because the x-ray equipment controls emulate control interfaces typically found on x-ray equipment, the simulation provides a realistic experience for the user. The x-ray equipment model may also allow users to change other information about the x-ray equipment, such as make, model, or year of manufacture.

The x-ray equipment model also processes the input received from the external control source. For example, the variations in C-arm movement, angulation, or collimation, are processed by the x-ray model to change the radiation characteristics that are being emitted by the equipment. This, in turn, changes the radiation metrics, feedback, and performance evaluation provided by the system.

In addition to specifying information about the x-ray equipment being used, system input 101 allows a user to specify a human exposure model, which specifies the location and structure of the anatomies of the patients being operated upon or individuals of a medical team during the simulation. The human exposure models may be realized as three-dimensional mesh models. These models may be generated by segmenting CT or MRI scans of real patients. The human exposure model may also include organs of the patient, including but not limited to the heart, brain, eyes, thyroid and gonads to calculate more accurate estimates of penetration, backscatter and organ dose. This may additionally be used to identify and highlight special areas of extra sensitivity, as different organs may have different sensitivities to radiation. Using three-dimensional mesh models of the patients enables an accurate determination of the distance between a part of the x-ray system (e.g., the x-ray tube or the image detector) and the patient's skin, which is an important factor in estimating the resulting radiation exposure.

In some embodiments, a patient-specific anatomy model may be created based on a CT or MRI scan of the patient. The CT or MRI scans are then used to determine the exact locations of different anatomical features. Such patient-specific models may be beneficial in scenarios where the patient would be very sensitive to radiation exposure and/or the exact anatomy is of vital importance, such as a pregnant or young patient. The patient-specific model is then used to simulate a real procedure, enabling the medical professional or team to practice how to best minimize the radiation for the particular patient in a safe and radiation-free environment. The visual feedback on expected radiation to the patient body and suggestions on procedural improvements during the practice run can then be used to minimize the actual radiation delivered to the patient during a real procedure.

The human exposure model may account for many different variations of patient anatomy and patient backgrounds, corresponding to various real-life situations, such as for example, patient age, size and shape, medical histories, weight, gender, or whether they are pregnant. The input to the human exposure model may come from obese/ underweight patients, males/females, pregnant women, newborns, children, adolescents, adults or elderly, or any combination thereof.

Radiation metric processor 102 calculates radiation metrics based on the x-ray equipment model, and human exposure model. Radiation metric processor 102 models how the delivered radiation would change as a result of changing input parameters. These radiation metrics are processed by the feedback system 103 and enable a user to determine how to adjust input parameters to change x-ray image noise and patient/medical team radiation exposure. The radiation metrics may also be used by the evaluation system 104 to evaluate a user's performance, and make recommendations as to how a user may reduce radiation exposure. The radiation metrics processor 102 may calculate various different metrics at various different reference points. The metrics may reflect current dose rates and cumulative dose rates. The metrics may be dependent on several input parameters that change during the course of a procedure.

A feedback system 103 provides information to the user based on the current and cumulative dose rates calculated by the radiation metrics processor. The information provided by the feedback system 103 translates the radiation metrics into values the user can relate to in a real-world setting or that may be useful for improving their understanding of the underlying principles of ionizing radiation. Specifically, the information may include simulated x-ray images, dosage indicators, dosage heatmaps, scatter radiation profiles, and timelines of radiation metrics.

In one embodiment, the feedback system 103 stores the radiation metrics in a data collection storage. The data collection storage may store the radiation metrics to provide as, for example, a report after the simulated x-ray procedure.

The x-ray images that are displayed to the user are generated by an x-ray imaging simulator. The x-ray imaging simulator generates an x-ray image that is altered to include noise associated with the x-ray equipment input parameters. The simulated x-ray images are generated by adding noise to a base x-ray image. The base x-ray image may be obtained from previous procedures, databases of pre-existing x-ray images, or modeled from CT and MRI scans. In a preferred embodiment, it may also be obtained from interfacing with an endovascular simulator. A level of x-ray image noise and contrast is calculated based on the current input parameters. The noise pattern is then applied to the image to give the effect of reduced or improved x-ray image quality.

In one aspect of the invention, an x-ray imaging simulator may include two-dimensional or three-dimensional overlays. For example, the x-ray imaging simulator may overlay the x-ray image with a mask. Masks are overlays of relevant areas or body parts, such as a vasculature, that help a user navigate through a procedure. Another type of overlay may be an image of a patient's actual anatomical body part. These images may be obtained before the actual procedure, for example with a CT scan, or, it may have been obtained during the procedure, for example, using rotational angiography or CBCT. The projected overlay can also be colored, to better distinguish it from the x-ray image. The image overlay may also be used with previous x-ray images and digitally subtracted from a current image to create "roadmaps" of a vasculature. The transparency of the overlaid image may be varied to display both the live x-ray image and the overlaid mask image at the same time. For images and for cine acquisitions, which have been captured with the mask image activated, a user may toggle the mask or subtracted image on or off, without having to make a new recording and exposing the patient to additional radiation. It may also be possible to take an already recorded image or frame from a cine acquisition and directly choose to use it as a mask image.

The x-ray image simulator may provide fluoro store functionality. Fluoro stores, or fluoro loops, store records of a certain limited number of fluoroscopic frames, either when activated or continuously throughout the procedure. The operator may then, when so needed, instead of recording a cine or DSA, choose to store the last fluoroscopic sequence from the fluoro store as a means of reviewing or documenting a certain step in the procedure. In this way, the use of the fluoro store avoids overuse of cine and DSA acquisitions. The x-ray imaging simulator provides fluoro store functionality by saving a number of the most recently viewed frames. The number of saved frames may be based on a predetermined time window, such as the last 30 seconds of live x-ray.

Feedback system 103 may further manage notifications to the user based on radiation metrics exceeding various threshold values. If during execution of the simulation a radiation metric approaches or exceeds a threshold, the simulation may notify the user. For example, warnings may be given when the cumulative peak skin dose, reference point air kerma, KAP and/or fluoroscopy time exceed certain thresholds. These warnings may be an audible warning, a flashing icon on the display, or a written message on a touch screen or tablet displaying which threshold has been exceeded, what the value of the threshold is and warning the user. The notification may also require the user acknowledge or confirm the notification.

The notifications may consist of a first notification, followed by subsequent notifications at every point when another additional fixed amount of radiation is exceeded. If the threshold for patient follow-up has been exceeded, another warning text may be added specifying that radiation induced injury may have occurred and that the patient should receive follow-up. The feedback system may provide instructions to the user to help avoid exceeding any of these thresholds.

Figure 2:
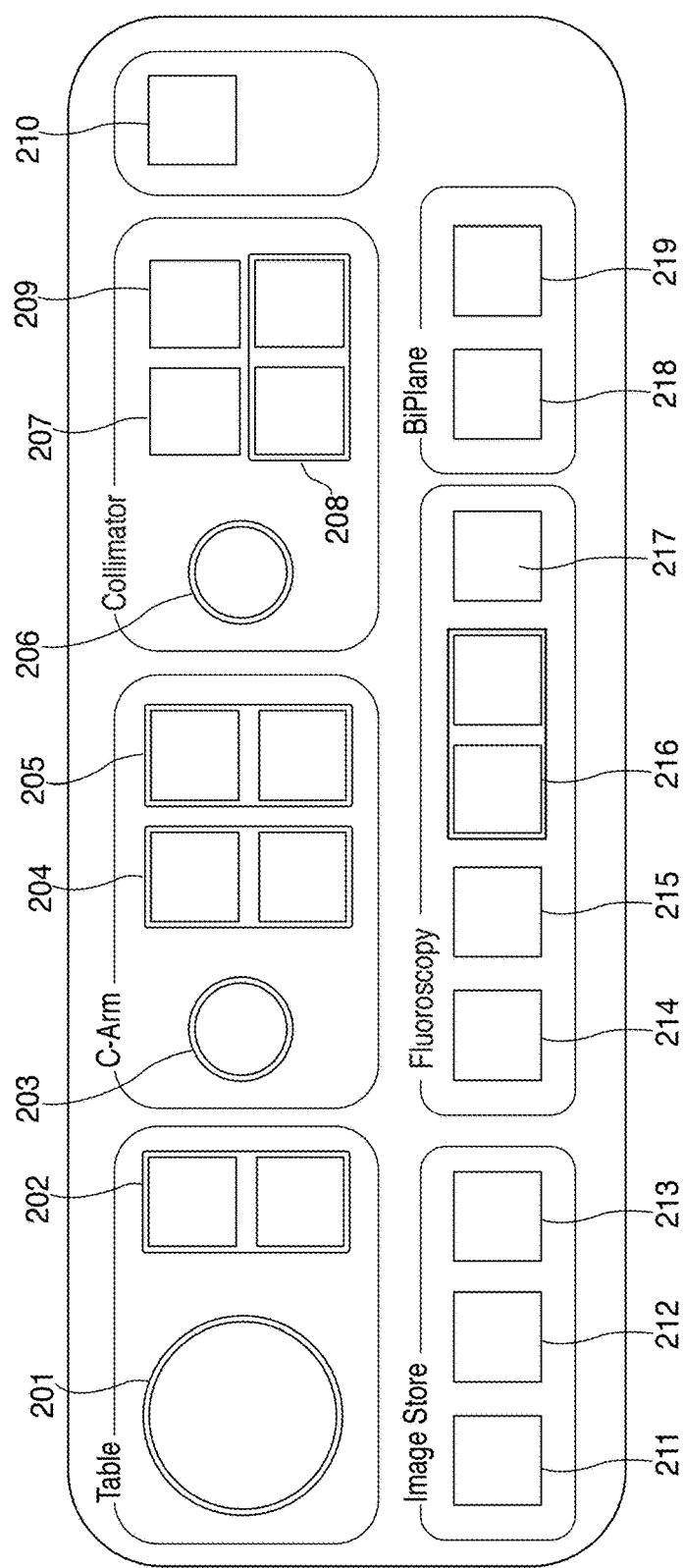
FIG. 2 shows a control box according to one embodiment of the invention.

FIG. 2 illustrates a system input having x-ray equipment controls according to one embodiment of the invention. The system input may include controls for the movement of the patient table, such as a control to move table's lateral position 201, and a control to move table height up/down 202. The system input may further include controls for the movement of the C-arm, such as a control for moving the c-arm gantry angle 203, moving the detector up/down 204, and changing the brightness level of the detector 205. The system input may further include controls for the collimation setting of the C-arm, such as the position of the collimator/wedge filters 206, a toggle for the use of collimator/wedge filters 207, a reset for resetting the position of collimator/wedge filters 208, and a control for adjusting the magnification level up/down 209. The system input may further include a toggle to enable a three-dimensional overlay 210, which can be used to overlay a semi-transparent previously obtained three-dimensional mask image of the vasculature onto the x-ray image. The system input may further include controls for the image store, such as a switch to enable the capture of fluoroscopic images 211, a switch for playing a series acquisition 212, and a switch to pause/step through a series acquisition 213. The system input may further include controls for the fluoroscopy settings, such as a switch to enable the capture of a mask image 214, a toggle for turning a roadmap on/off 215, a control to change the mask weight up/down 216, and a toggle to change dose level to low/normal/high 217. The system input may further include controls for the biplane settings, such as a toggle to choose between frontal/lateral/biplane positioning of the c-arm 218, and a toggle to choose between activating frontal/lateral/biplane fluoroscopy 219.

In one embodiment of the invention, the selection and arrangement of the x-ray equipment controls emulates the selection and arrangement of controls that are found on real vendor-specific control boxes of operable x-ray equipment. For example, the x-ray equipment control box may be produced with the same controls and arrangement as a Siemens, Philips, General Electrics, or Toshiba x-ray machine. Thus, a user controlling the x-ray equipment would feel as if he or she were operating on a real Siemens, Philips, General Electrics, or Toshiba x-ray machine. In this way, the system may enhance the realism and hands-on training component of the simulation. In another embodiment of the invention, the selection and arrangement of the controls may be independent or unrelated to a specific vendor. That is, the control box can be based on functionality that is common to commercial x-ray systems. The common controls may include, but are not limited to, table and c-arm movements, image, x-ray, roadmap, fluoro store, collimation, wedge filter and biplane settings.

In other embodiments, x-ray equipment controls may be the actual control boxes from x-ray equipment. Some x-ray equipment systems allow control boxes to be detached from the system. These detached control boxes may be adapted to provide input into the simulation system. For example, the control interface from a Siemens, Philips, General Electrics, or Toshiba x-ray machine may be adapted to communicate to the x-ray equipment model.

Figure 3C:
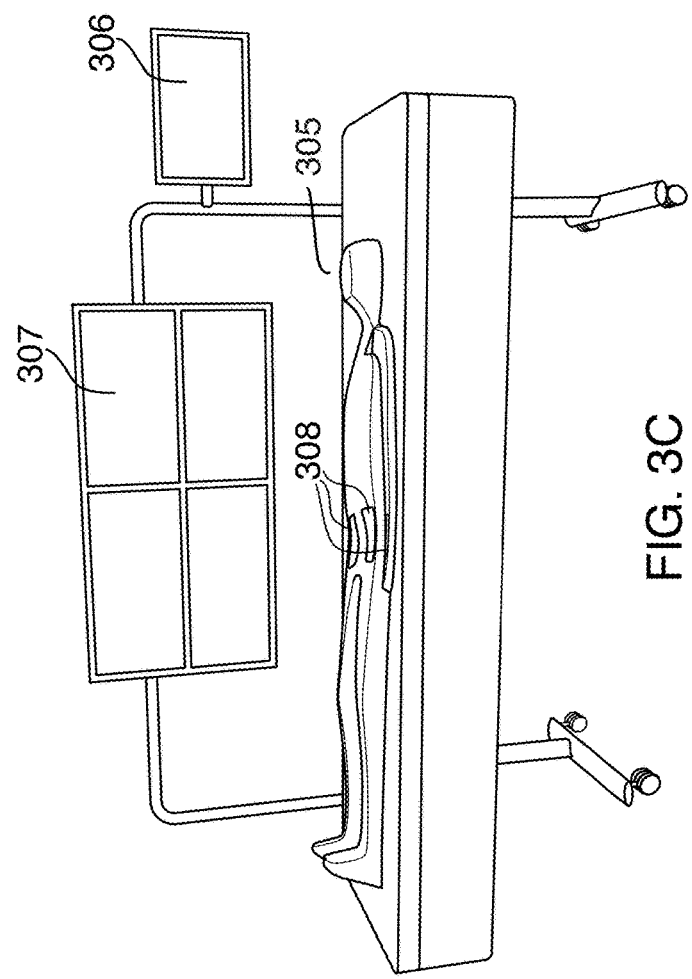
FIGS. 3A, B and C show examples of external control input devices that can be used with the simulation according to one embodiment of the invention.
Figure 3A:
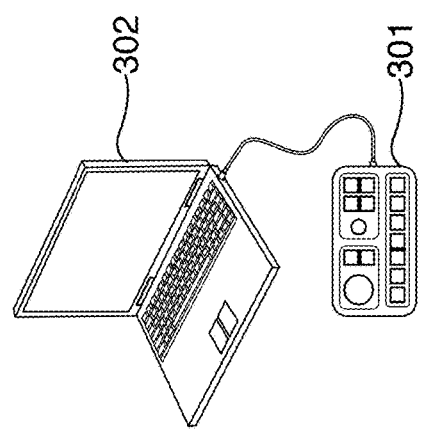
Figure 3B:
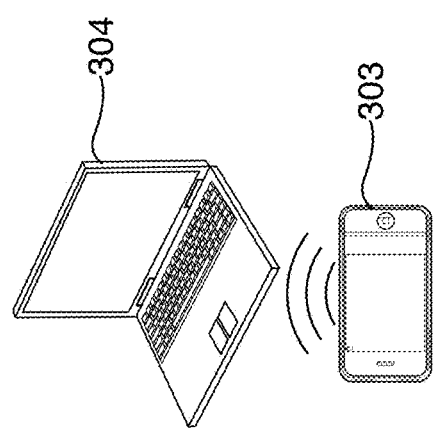

FIGS. 3A, B and C depict additional embodiments where x-ray equipment controls are implemented with tablets, smart phones, touch screen monitors, and similar devices. In FIG. 3A, x-ray equipment controls 301 may be a physical control box with controls arranged to emulate a real vendor-specific x-ray machine, such as a Siemens, Philips, General Electrics, or Toshiba x-ray machine. The control box may also be vendor-independent, providing a selection of controls and in an arrangement that is not associated with any particular vendor. The control box 301 may be coupled to a computer 302 or 304 where the radiation metrics processor, feedback system, and evaluation system may execute. In FIG. 3B, x-ray equipment controls 301 may be implemented with a tablet, smart phone, or similar mobile device 303. The radiation metrics processor may execute in the computer 302 and 304, in the control box 301 or in the mobile device 303. The controls in a mobile device may be implemented with software and a touch screen. Use of a mobile device enables a user freedom to move about the system. Further, the user interface may be programmed to provide different selections of controls and in different arrangements, for example to accommodate vendor-specific control designs. Thus, the simulation system may be adapted when vendors update or change control designs.

FIG. 3C illustrates a medical simulator 305, and touchscreens 306 and 307. The medical simulator 305 includes a human-shaped figure. The human-shaped figure may include one or more openings 308 that may be used to simulate treatment. The touch screens 306 and 307 may be used to receive user input and display radiation metrics, feedback, and evaluation during a procedure. In other embodiments, the medical simulator and display in FIG. 3C may be used with the control box 301 or mobile device 303 as described above. The radiation metrics processor may execute in the medical simulator 305, or touch screens 306 and 307.

Figure 4C:
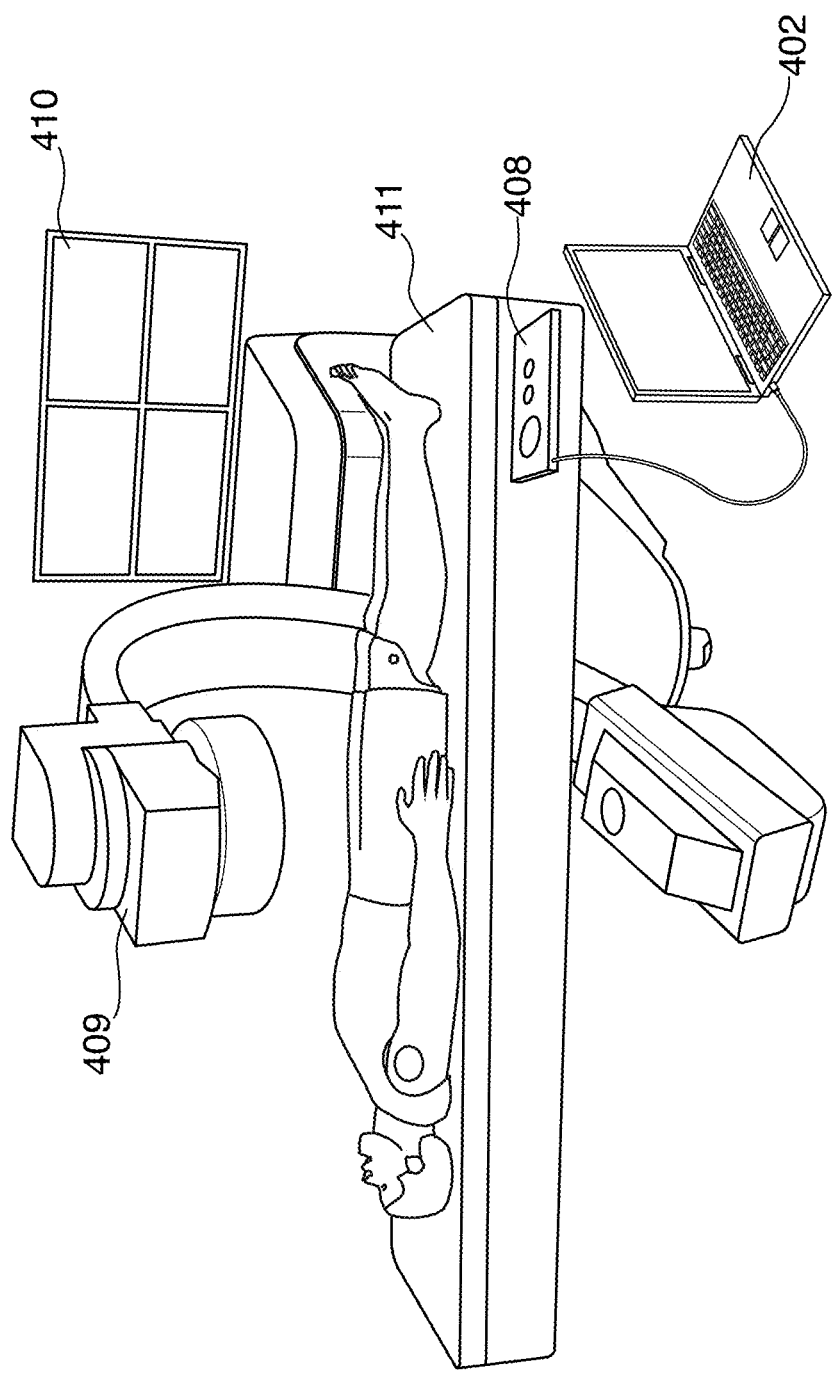
FIGS. 4A, B and C show the radiation protection simulation system integrated with other medical simulators according to one embodiment of the invention.

FIGS. 4A, 4B, and 4C illustrate various embodiments of simulators that may be coupled to the system input. The different simulators provide varying levels of realism and portability to the user.

According to one embodiment shown in FIG. 4A, a system input 401 and display 402 may be coupled to a portable medical simulator 403. The medical simulator may optionally have an integrated system input 401. The system input 401 includes controls for manipulating x-ray equipment as described above. However, because the simulator 403 is not coupled to a physical x-ray machine, display 402 simulates where the x-ray equipment would be positioned in response to input provided by the user. As shown in FIG. 4A, the display 402 may also simulate the x-ray image that would be generated by the x-ray equipment under current input parameters. Portable simulator 403 may be used, for example, to provide simulations of endovascular procedures, such as angiography and interventional training procedures. A simulator for endovascular surgery is a system that tracks the motion of the medical instruments through a separate hardware device, and the detected motion is translated into movements of virtual instruments inside a virtual model of the patient. An emulated x-ray image of the instruments moving inside the virtual patient is shown on a computer screen, allowing the physician to train on the steps of a specific intervention or the particularities of a certain procedure.

In one embodiment where portable simulator 403 is used to simulate endovascular procedures, the simulator may include an opening 404 for simulating access to an entry point into the cardiovascular system. For example, the opening 404 may be used to simulate catheterization of the right coronary artery from a right radial artery. The user may feed a real guidewire or catheter through the opening 404; as the guidewire or catheter is furthered through the vascular pathway, display 402 will show where the guidewire or catheter would be located if the user were operating on a real patient. In this way, the portable simulator 403 may be used to train professionals in angiography or endovascular intervention.

According to another embodiment shown in FIG. 4B, a system input 405 and display 402 may be coupled to a human patient simulator 406. The system input 405 and patient simulator 406 provide an additional level of realism, by providing a realistic selection and arrangement of control inputs for x-ray equipment and a realistic full body mannequin. The full body mannequin may include one or more openings 407. Similar to the portable medical simulator 403, the patient simulator 406 allows users to simulate different types of x-ray guided medical procedures. Display 402 simulates where the x-ray equipment would be positioned in response to input provided by the user. As shown in FIG. 4A, the display 402 may also simulate the x-ray image that would be generated by the x-ray equipment under current operating conditions. Thus, like the portable simulator 403, patient simulator 406 provides radiation training for x-ray guided medical procedures.

According to another embodiment shown in FIG. 4C, a system input 408 and x-ray machine 409 may be coupled to a display 402 or 410. The x-ray machine 409 may be an actual x-ray machine used in a medical setting, and operated with actual system input 408. For example, the x-ray machine may be a mobile or stationary C-arm machine used in performing fluoroscopic-guided procedures. The system input 408 may control the movement and settings of the C-arm over the table and human patient simulator, in response to the control signals provided at system input 408.

While the x-ray machine 409 moves in response to the system input 408, the x-ray machine does not emit radiation. The positions and operating settings the user sets at system input 408 are used to derive a simulated image shown on a display 402 or 410. The simulated image shown on display 402 or 410 represents the x-ray image that would have been generated by the x-ray machine 409 at that position and under those particular settings during a real procedure. In this way, the use of a real machine 409 and system input 408 provide yet another dimension of realism for the user. Further, the x-ray imagery shown to the user may be generated without using ionizing radiation; thus a user (or team) can train on a specific medical procedure in a real operating room environment, without exposing a patient, or him- or herself to harmful radiation. In another embodiment of the invention, the simulator 409 may be set up inside an actual operating room of a hospital or health care facility.

In one aspect of the invention, the x-ray machine 409 is coupled to a table 411. The table may be a conventional catheterization table or operating table. If the table 411 is an operating table, the simulation system may be used to simulate a hybrid procedure, which combines x-ray imaging techniques with open surgery performed on an operating table. Such hybrid systems provide training for x-ray guided and open surgical procedures, and therefore, can be used for team and cross-specialty training.

Figure 5:
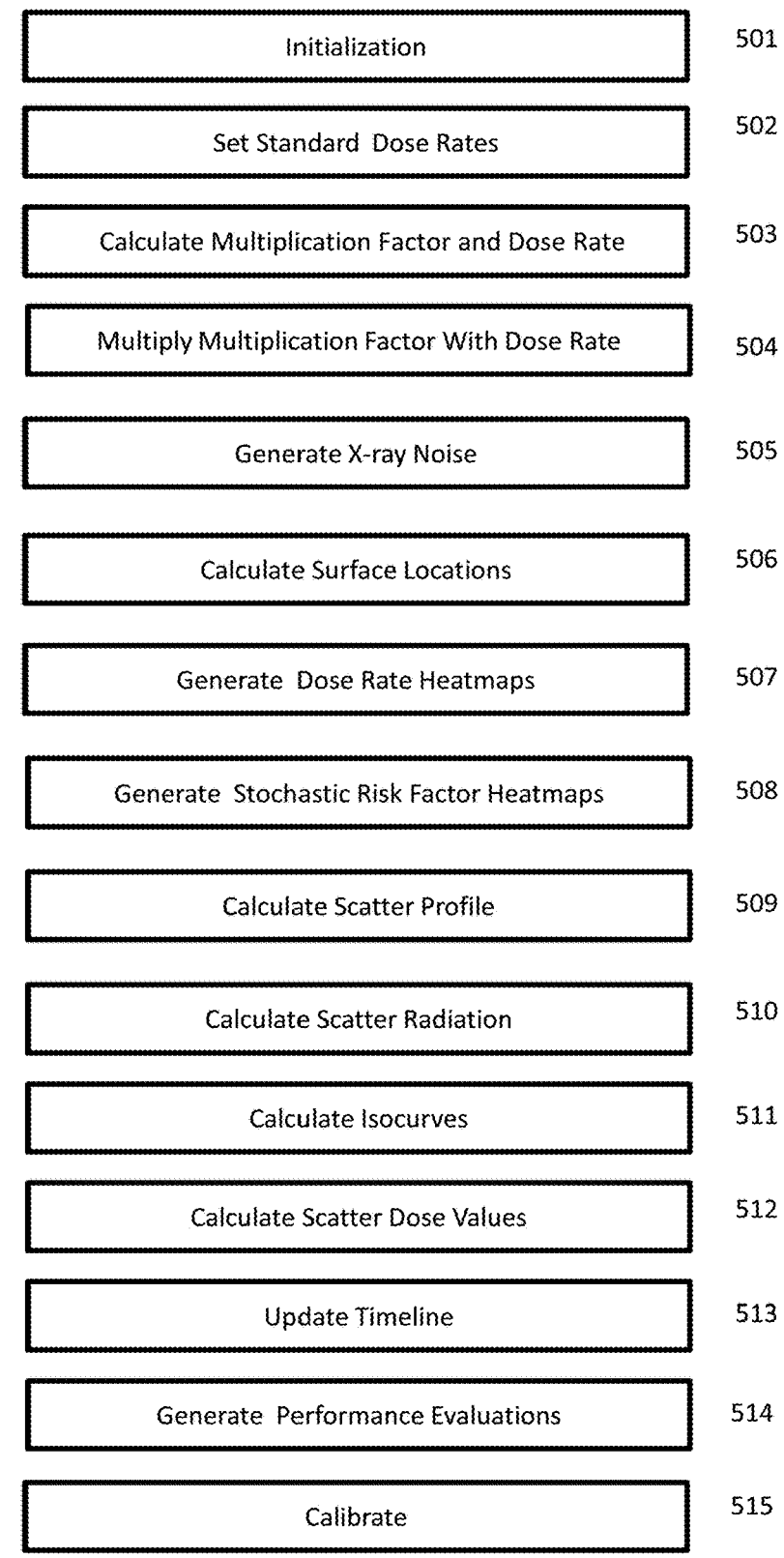
FIG. 5 is a flowchart of a method for calculating radiation metrics according to one embodiment of the invention.

FIG. 5 shows a method for calculating radiation metrics according to one embodiment of the invention. The procedure illustrated in FIG. 5 calculates radiation metrics by initializing IRP and KAP dose rates according to a standard model, and then scaling the dose rates according to changes in different input parameters. Some of the steps shown in FIG. 5 are optional, and need not be performed to execute the simulation; optional steps shown in FIG. 5 are used to generate metrics that users may be beneficial in incorporating into the simulation.

The radiation metric data calculated by the radiation metric processor includes a number of metrics that may be calculated at several different reference points. In one embodiment, the metrics are calculated at the "interventional reference point" (IRP). The IRP is a reference point typically measured to be 15 cm in front of the "isocenter" towards a radiation source, which is generally located underneath the patient table. The "isocenter" is the rotational center of the C-arm, i.e., the point that always stays in the center of view regardless of the angle of the C-arm. The IRP may be used as an approximation of the location of a patient's skin, and may be used to calculate the air kerma rate at the IRP. Changing the table height does not change the position of the IRP, which can cause substantial discrepancies between the estimated skin dose at the IRP and the real skin dose that the patient has received.

In accordance with other embodiments of the invention, the dose rate may be calculated at an FDA dose point (FDP). The FDP may be a point located 30 cm in front of the flat panel detector. When changing the detector height, this point moves, which can result in a number of situations where the IRP and FDP coincide, where the IRP is in front of the FDP, or where the FDP is in front of the IRP. Occasionally, the FDP may be used as a reference point for limiting the maximum allowable dose rate of a system. For example, the fluoroscopy dose rate at the FDP may be limited to 88 mGy/min. For imaging systems with automatic regulation of output dose, i.e. using Automatic Brightness Control (ABC) or Automatic Dose Regulation Control (ADRC) to maintain close to constant image quality by the detector, this dose rate limit may then result in a decrease in x-ray image quality once the limit has been reached. In another embodiment, the actual position at which the top surface of the patient table intersects with the central beam may be used as a reference point.

When a reference point has been determined, the radiation metric processor may calculate metrics using the reference point and specific information about the x-ray equipment, such as the locations of the source and table from the x-ray equipment model. The radiation metrics may include KAP rate, air kerma rate at the IRP, peak skin dose (PSD), and corresponding accumulated metrics. Radiation metric data may further include patient heatmaps, scatter radiation maps, and isocurves. Because the different radiation metrics may change over the course of the procedure, these radiation metrics may be saved at different points in time, creating a timeline of radiation metrics.

In step 501, radiation metric data is initialized to zero, and radiation metric thresholds may be set. Radiation metric thresholds are values for certain metrics, such as dose rate, that may be used throughout the simulation to trigger alarms or provide feedback and performance evaluation. The thresholds may be set to reflect government regulations, hospital policies, and technical thresholds that are in place to control the boundaries within which an x-ray system may operate. For example, FDA rules cap the dose rate at the FDA dose point at a maximum of 88 mGy/min for live fluoroscopy on systems with ADRC. However, this limit does not apply to special high dose modes such as the high fluoro dose setting, nor to cine or DSA acquisition, where rates may reach levels many-folds higher than this threshold. Most imaging systems also have protocols for specific procedures that set the rate limits lower than this FDA threshold. Thresholds may also change or be set during the course of a procedure.

In step 502, a standard IRP dose rate and standard KAP rate $k_{ref}$ is set by the system. As described above, the simulation may include an input for setting any number of input parameters, including the movement and angulation of the table and C-arm machine, the fluoroscopic pulse rate of the x-ray machine, fluoroscopic dose level (low/normal/high), cine acquisition (on/off), cine acquisition frame rate, C-arm detector height, collimation (square or round), the number of wedge filters being used, the magnification or Field of View (FOV), the use of Digital Subtraction Angiography (DSA), the dose protocols being used for specific procedures, x-ray tube voltages and currents, the use of beam shaping filters, the use of automatic dose rate control (ADRC), the location of the radiation source (above or below the patient table), or the use of an image intensifier instead of flat panel. The standard IRP dose rate and standard KAP rate are calculated based on a predetermined set of these parameters having a predetermined value. For example, in one embodiment, the standard IRP dose rate and standard KAP rate are calculated based on the following set of parameters and may have the following initial set of values:

TABLE 1

| | |
|---|---|
| Patient table | The surface of the patient table is positioned at the isocenter of the C-arm |
| C-arm | The C-arm is positioned directly anterior-posterior (AP) |
| Patient thickness | The patient thickness is 20 cm |
| Fluoro dose level | The fluoro dose level is set to "normal" |

TABLE 1-continued

| | |
|---|---|
| Fluoro pulse rate | The fluoro pulse rate is set to 30 pulses/second (p/s) |
| Cine acquisition | The cine acquisition is "off" |
| Cine acquisition frame rate | The cine acquisition frame rate is set to 30 frames/second (f/s) |
| SID | The SID is 120 cm when the detector is at its maximum distance from the source |
| FOV | The field-of-view is 23 cm |
| Collimators | The collimators are completely removed |
| Wedge filters | The wedge filters are completely removed |
| DSA | The DSA mode is turned off |

As explained above, during the course of a procedure, the user may adjust or change some of these input parameters. And, as explained above, a change in the input parameter may change the radiation dose rate delivered to the patient and team, as well as quality of the x-ray image generated by the machine. According to some embodiments of the invention, the change in parameter value may be ignored.

In one embodiment, the thresholds described above may be dependent on these parameters. For example, the relationship between patient thickness, low/normal fluoro dose setting, pulse rate and the delivered patient dose rate determines at what point these dose thresholds are reached. Using a higher pulse rate may for example, result in the threshold being reached for a smaller patient thickness than if a lower pulse rate were used. Using the "low" fluoro dose level setting will also lower the threshold and cause the threshold to be reached even earlier. Thus, a change in the parameter value may result in a change in threshold value. During simulation, a comparison between any set thresholds or threshold profiles may be displayed. In addition, during or before simulation, the simulator may display instructions to a user relating to how to remain within any thresholds or threshold profiles. For example, if the current dose rate is too high, the simulator may instruct the user to switch to a low dose setting from a normal setting. Thresholds may also be used to cap certain parameter values or settings once a threshold has been reached. As a result, the simulation may prevent the output dose rates from increasing, and image quality may deteriorate. For example, after the FDA dose point limit of 88 mGy/min for live fluoroscopy has been exceeded, the level of x-ray image noise during the simulation may start increasing. Or, after a dose limit of 1400 mGy/min has been exceeded for cine acquisition or DSA, the level of x-ray image noise in the recorded acquisitions may likewise increase.

In one aspect of the invention a model may associate a change in the input parameters with a change in the radiation exposure metrics. According to some embodiments of the invention, the variations in parameter values may be used to modify the radiation exposure metrics by calculating a multiplication factor and current dose rate in steps 503 and 504. In step 503, multiplication factor is calculated, and in step 504, a current IRP dose rate and current KAP rate are calculated by scaling an IRP dose rate and KAP rate by a multiplication factor. A current dose rate $d_t$ may be expressed as:

$$d_t = k_{ref} \prod_i f_i(w_i, p_t),$$

where $$f_i(w_i, p_{ref}) = 1$$

where $d_t$ is the dose rate at time-step t, $k_{ref}$ is the base dose rate described above (i.e., the expected dose rate for a pre-defined set of parameters having a predetermined set of values $p_{ref}$), i is an index covering all parameters that influence the dose rate delivered to the patient, $f_i(w_i,p_t)$ is a multiplication factor calculated as a function of a weight $w_i$, and parameter values $p_t$. Weight $w_i$ can be used to calibrate each factor-dependent function to the measured dose rate of a real operable x-ray system, and $p_t$ is a vector of all input parameter values at time-step t. The requirement of the factor-dependent functions to fulfill $f_i(w_i,p_{ref})=1$ guarantees that $d_t=k_{ref}$ when $p_t=p_{ref}$.

The dose rate $d_t$ above can be used to calculate various dose rates, such as air kerma rate at the IRP, KAP rate, air kerma rate at the FDP, air kerma rate at the table surface and actual skin dose. Some categories of dose rates may not be affected by certain parameters. For example, collimation or wedge filter parameters may affect the KAP dose rate, but not the air kerma rate at the IRP. Thus, the $k_{ref}$ values and weights for different categories of dose rates may be different.

Factor functions $f_i(w_i,p_t)$ are generated using physical models and empirical data to create a system that accurately adjusts a dose rate when input parameters of the simulation are changed. A detailed description of the factor function $f_i(w_i,p_t)$ for several parameters according to different embodiments of the invention are described below.

In one embodiment of the invention, a factor function may be based on a parameter "path length." "Path length" is the length an x-ray beam travels through a human body. The path length of a patient can be affected by three sub-factors: (i) the patient's thickness (e.g., the thicker patient, the longer the path length); (ii) the angle of the c-arm (e.g., the more acute angle, the longer path length, because a human body is normally wider than it is thick); (iii) the part of the body the x-ray beam is traveling through (e.g., the abdomen is thicker than the arm). The path length through the body can be calculated using these three sub-factors. Modeling patient thickness in this way, enables a user to easily simulate patients of different shapes, genders and sizes, and to account for horizontal table movements and patient positioning on the table.

In some embodiments implementing the "path length" factor, the path length may be calculated by modeling the human body with as a three-dimensional triangle mesh object, and treating the x-ray beam as a straight line passing through mesh object. Ray tracing may be used to identify all triangles that intersect the ray. The internal lengths between these intersection points may then be summed to obtain the total path length through the triangle object.

In general, an x-ray system fitted with ADRC tries to keep a received dose at the detector constant, and therefore, a longer "path length" through the body will result in an increase of emitted dose in comparison to a shorter one. Likewise, theoretical models based on the assumptions that the human body is mostly made up of water suggested that an increase in patient thickness of about 3 cm from the "normal" 20 cm would result in twice the necessary entrance dose. Similarly, physical and geometric models suggested that there would be a 360% increase in entrance dose if the patient's body was rotated at a 45 degree angle from the anterior-posterior (AP) view, and a 700% increase at 55 degrees (assuming a 20 cm thick and 40 cm wide patient with a perfectly oval body). However, empirical studies show that the actual entrance dose values differ significantly from the theoretical values above, because the theoretical values are based on the inaccurate premise that the body is mostly made up of water. Indeed, the body is not only made up of water but is also made up from bones, organs, and other organic materials. The empirical studies showed that skin dose rate may increase from 0.4 to 5.6 (a factor of 14:1) as the path length increases from 12 to 36 cm (a factor of 3:1).

In order to account for the discrepancy between theoretical models and empirical data, the following factor-dependent function to model path length may be used:

$$f_i(w_i, p_t) = 2^{\left(\frac{l_t - l_{ref}}{w_i}\right)}$$

where $l_{ref}$ is the reference path length, $l_t$ is the path length at time point t, and $w_i$ is the calibration weight, which in this case would correspond to the increase in path length that would cause the radiation dose to double.

For example, to correspond to the theoretical values, a reference path length $l_{ref}=20$ cm and a calibration weight of $w_i=3$ cm may give a dose multiplication factor $f_i=1$, so that a later increase in path length of 3 cm ($l_t=23$ cm) would yield $f_i=2$. Similarly, a reduction in path length of 3 cm ($l_t=17$ cm) would then yield $f_i=0.5$ and so on.

Alternatively, the weight may be adapted to empirical values from real world equipment. In this example, setting the weight to $w_i=6.304$ would yield the empirically measured value of increasing dose rate by a factor 14 when the path length increases by 24 cm.

Special consideration needs to be taken if the path length becomes very low or zero (e.g., when the beam is completely outside of the body). If the path length becomes very long, certain limiting factors on the x-ray tube and dose regulations may be implicated, resulting in dose rate thresholding and a decrease in image quality which are discussed in more detail below.

In some embodiments implementing the "path length" factor, the path length factor may model the individual beams inside the field of view. In real environments, x-ray beams at various points inside the field of view can have different path lengths from the central x-ray beam. The path length of each beam would then be calculated in the same way as has been described above for the central beam, a separate multiplication factor contribution (depending on the number of x-ray beams considered) calculated for each different path length, and these contributions would then be summed together to yield the final multiplication factor.

In one embodiment of the invention, a factor function may be based on a parameter "fluoroscopic pulse rate." A reduction to half pulse rate would theoretically reduce the air kerma dose rate at the IRP by about half. For example, a reduction from 30 p/s to 7.5 p/s should result in a dose saving of 75%.

The following factor-dependent function to model fluoroscopic pulse rate may be used:

$$f_i(w_i, p_t) = \frac{p_t}{w_i \cdot p_{ref}}$$

where $p_{ref}$ is the reference pulse rate, $p_t$ is the pulse rate at time point t, and $w_i$ is the calibration weight, which in this case would be equal to 1 for the pure physics based model.

However, empirical studies have shown that the entrance skin dose rate may exhibit a more moderate reduction, where lowering from 30 p/s to 15 p/s only reduced the dose by 22% and to 7.5 p/s by about 50%, due to compensation of tube current by the ADRC to maintain image quality. The weight may therefore be adjusted to reflect this real-life measured relationship by setting $w_i=2$.

An ADRC may be configured to explicitly operate either with a linear dose reduction strategy (with marked loss in image quality) or a balanced strategy (with less loss in image quality but also less dose reduction). Additional input parameters may therefore also be incorporated into a more complex version of this model.

Based on this information, an adequate simulated radiation exposure model for fluoroscopy pulse rate may therefore build on the balanced image quality values. For example, with the reference pulse rate set to $p_{ref}$=30 p/s and the calibration weight set to $w_i$=2, lowering the pulse rate to $p_t$=15 p/s would give an air kerma dose rate factor of $f_i$=0.75, and lowering it even further to $p_t$=7.5 p/s would yield $f_i$=0.5 and so on.

In one embodiment of the invention, a factor function may be based on a parameter "fluoroscopic dose level." Many modern systems offer a quick setting for the operator to reduce the fluoroscopic dose rate when the situation does not require the same high image quality. Using this option will also increase image noise. Sometimes, there is also a setting for increasing the dose during certain critical parts of the procedure, or in difficult imaging situations. Typically, the lower dose rate setting may reduce the emitted dose to 50% of the normal one, whereas the higher dose rate setting may double the dose compared to the normal dose.

The following factor-dependent function to model fluoroscopic dose level may be used:

$$f_i(w_i, p_t) = \begin{cases} 1/w_i & \text{mode = low} \\ 1 & \text{mode = normal} \\ w_i & \text{mode = high} \end{cases}$$

where $w_i$ is the calibration weight, which in this case would be equal to 2, since the empirically measured values would be expected to follow the theoretical ones. The standard reference value would correspond to the dose level being set to "normal".

As part of the radiation simulation, a choice may therefore be added to toggle between low, normal, and high dose rate settings. However, other intermediate settings or other combinations of the intermediate settings may be used (e.g., only low and normal). The low dose setting may reduce the emitted dose to 50% (or another value) and the image noise would increase correspondingly. The high dose setting may increase the emitted dose by 100% (or another value) and reduce the image noise correspondingly.

When the high dose mode is used, a distinct continuous signal may sound in the radiation simulator to warn the operator of the high dose (however, it should be possible to turn this off in configuration). If the high dose mode is used continuously for more than 20 seconds or another set time period, it may automatically revert to normal mode.

In one embodiment of the invention, a factor function may be based on a parameter "cine acquisition." For cine acquisitions, dose levels are much higher than for live fluoroscopy, in order to deliver good image quality. Generally, most x-ray cinefluorographic units are calibrated such that the per-frame dose for such acquisition is approximately 15 times greater than for fluoroscopy. In some cases, acquisition may be 10-15 times greater. Hence, a simulated radiation exposure model may use a value of 15 (or another value) times the fluoroscopic dose when using cine acquisition.

The following factor-dependent function to model cine acquisition may be used:

$$f_i(w_i, p_t) = \begin{cases} 1 & \text{cine = off} \\ w_i & \text{cine = on} \end{cases}$$

where $w_i$ is the calibration weight, which in this case could be set equal to 15 to correspond with the empirically measured values. The standard reference value would correspond to the cine acquisition being "off".

Although the "normal" or "low" fluoroscopic dose level setting normally does not change the delivered dose rate when acquiring a cine series, the factor dependent function may be modified to include such effects during an acquisition. Typically, however, the factor-dependent functions for both fluoroscopic dose level and pulse rate would be omitted from the total dose rate formula when cine acquisition is set to "on".

In one embodiment of the invention, a factor function may be based on a parameter "cine acquisition frame rate." The cine frame rate setting would result in the same proportional changes as changing the pulse rate does for fluoroscopy, and may therefore be modeled in the same way:

$$f_i(w_i, p_t) = \frac{p_t}{w_i \cdot p_{ref}}$$

where $p_{ref}$ is the reference cine frame rate, $p_t$ is the cine frame rate at time point t, and $w_i$ is the calibration weight, which would be equal to 1 for the pure physics based model, but in a more realistic empirically derived model may be set to 2 using the exact same argumentation as for fluoroscopy pulse rate.

In one embodiment of the invention, a factor function may be based on a parameter "C-arm detector height (SID)." Studies suggest that raising the source image distance (SID) from 105 cm to 120 cm increases air kerma dose rate at the IRP by approximately 30%, based on an inverse quadratic relationship to distance. Other studies suggest that an additional 10 cm air gap between the detector and the patient results in a 20-38% increase in skin dose.

A factor-dependent function for this may be expressed as:

$$f_i(w_i, p_t) = \left(\frac{s_t}{w_i \cdot s_{ref}}\right)^2$$

where $s_{ref}$ is the reference SID, $s_t$ is the SID at time point t, and $w_i$ is the calibration weight, which in this case would be equal to 1 for the pure physics based model. Raising the detector by a certain distance results in the exact same increase in SID.

In one embodiment of the invention, a factor function may be based on a parameter "collimation." Adjustable circular or rectangular collimators are normally placed between the radiation source and the KAP reader and effectively reduce the total emitted dose to the patient by an amount proportional to the non-collimated area. While the total emitted radiation dose is reduced, the air kerma rate at the IRP will be roughly constant because the IRP is located in the center of the collimated window. In real environments the IRP dose rate can even increase due to compensation by the ADRC. In a radiation simulator, therefore, the ratio of the non-collimated area to the full area may determine the total dose reduction, which may in turn affect the KAP value calculation, but not necessarily the skin dose at the IRP. For example, if the collimators cover 30% of the full view, the KAP rate may likewise be reduced by 30% while the air kerma rate at the IRP remains unchanged.

Since the air kerma rate at the IRP is typically not affected much by the collimator setting, a radiation simulation model may exclude this factor-dependent function altogether. However, another similar factor function for KAP rate, which would indeed need to account for this control parameter, is instead provided below:

$$f_i^{KAP}(w_i, p_t) = \frac{a_t}{w_i \cdot a_{ref}}$$

where $a_{ref}$ is the reference non-collimated area, $a_t$ is the non-collimated area at time point t, and $w_i$ is the calibration weight, equal to 1 for a pure physics based model.

In one embodiment of the invention, a factor function may be based on a parameter "wedge filters." In addition to the main collimator blades, there are often various ways of using semitransparent collimators in combination with the primary collimators. Main collimators will normally only reduce the total emitted dose and consequently affect KAP rate. The semitransparent collimators often are formed as a wedge with a varying thickness across the collimator blade (so that the edge of the blade will create a smooth transition on the x-ray image) and are used to refine the primary rectangular collimation, and equalize contrast differences in the image. They are therefore also frequently known as wedge or equalization filters. They may have different shapes (e.g., rectangular, circular, semi-circular, oval, triangle shaped, or a combination thereof) but are on modern x-ray systems typically used in pairs, with one left and one right filter that are inserted from each side and may also be rotated to shield a diagonal part of the view.

A simulation model may account for the dosage change due to the use of semi-transparent collimator materials by changing the dose rate accordingly. Determining the level of reduced radiation due to wedge filters can be complex since the collimator blades are not uniform in thickness, may have different materials and shapes, and can be overlaid with each other. Additionally, the position of the main collimator blades may vary. In some studies, equalization filters were found to at least attenuate radiation by a factor 1:6. Some studies suggest a large variation in values for specific x-ray systems, and other studies have even shown that the air kerma and KAP rates may increase when a wedge filter is inserted, due to compensation by the ADRC.

One factor function for this parameter to yield KAP rate may be expressed as:

$$f_i^{KAP}(w_i, p_t) = \frac{a_t^{coll} - a_t^{filter}}{a_t^{coll}} + \frac{a_t^{filter}}{w_i \cdot a_t^{coll}}$$

where $a_t^{coll}$ is the non-collimated area at time point t, $a_t^{filter}$ is the non-collimated and filtered area at time point t, and $w_i$ is the calibration weight, in this case equal to 6 for an empirically based model. The model may also account for an increase in radiation as a result of inserting a wedge filter, in the example above meaning that $w_i$ would be set to a value below 1.

A more complex model may furthermore account for the effect of stacked primary and/or secondary collimators, such that they may be rotated or translated to form a resulting shape or transparency. This may be accomplished by dividing up the factor function into several parts, with each part corresponding to a particular geometrical area of overlap and a certain degree of transparency. The attenuation through each such geometrical part would then be calculated and the contributions from all areas summed together across the whole irradiated area. It may also in the same way account for finger filters or collimators, which are inserted into the center of the x-ray beam instead of from the sides.

In one embodiment of the invention, a factor function may be based on a parameter "magnification." Traditionally, the magnification level was altered by changing the field-of-view (FOV) of the x-ray beam and would then cause a change to the air kerma rate at the IRP that followed the inverse square law, with the KAP rate staying approximately constant. Thus, a simulation model may account for this behavior and calculate the radiation dosage in a similar manner when such a system is simulated.

However, modern imaging systems often allow noise levels to increase slightly to alleviate the effect on dose rate and then rather follow a linear relationship with FOV rather than a quadratic one. This would then also cause the KAP rate to decrease with higher magnification. Thus, a simulation model may account for this behavior and calculate the radiation dosage in a similar manner when such a system is simulated.

As a further complication, the highest magnification levels of flat panel detectors are on some systems obtained digitally with even higher dose savings or no change in dose at all compared to the next lower magnification level. Such a behavior may likewise be modeled in an extended factor function.

This parameter may be modeling using a linear relationship for both air kerma rate at the IRP and KAP rate as a compromise between all of the different factors above. This is illustrated in the factor-dependent function formulas for both air kerma and KAP rates below:

$$f_i(w_i, p_t) = \frac{v_{ref}}{w_i \cdot v_t}$$

$$f_i^{KAP}(w_i, p_t) = \frac{w_i \cdot v_t}{v_{ref}}$$

where $v_{ref}$ is the reference FOV, $v_t$ is the FOV at time point t, and $w_i$ is the calibration weight, which may be different for air kerma and KAP, but is equal to 1 for both in this case.

For example, in the exemplified radiation simulation model, if $v_{ref}=23$ cm and $w_i=1$ for both air kerma and KAP rate, a change in FOV to $v_t=15$ cm would give an IRP dose rate factor $f_i=1.5$ and a KAP rate factor $f_i^{KAP}=0.65$.

The image noise level may also be assumed to increase linearly in the same fashion as the air kerma dose rate at the IRP. Alternatively, the image noise level may follow a more complex relationship (e.g., exponential, log).

In one embodiment of the invention, a factor function may be based on a parameter "Digital subtraction angiography (DSA)." DSA is a technique used to more clearly distinguish the blood vessels from other anatomical structures in the x-ray image during a procedure. It is done by injecting contrast medium into the vasculature, capturing a mask image where the vessels are filled with contrast medium, and then subtracting this mask image from later images. Because the subtraction process accentuates image noise, it is necessary to counter this effect by acquiring each of the original images at a substantially (as much as 20-fold) higher dose per frame. The increased dose per frame may be partially offset by the ability to employ slower frame rates. However, procedures that use digital subtraction imaging generally have larger aggregate radiation doses than those that use unsubtracted cinefluorography, even up to 325 times more dose per frame compared to low-dose fluoroscopy. Some studies suggest even larger differences, with dose rates of 25-50 times of those that can be expected with unsubtracted cine acquisition.

To account for DSA, a simulator model may increase the air kerma rate at the IRP compared to normal-dose fluoroscopy by a factor 150, or 10 times (or another value) as much as an unsubtracted cine run. This can be expressed as the following factor-dependent function:

$$f_i(w_i, p_t) = \begin{cases} 1 & DSA = \text{off} \\ w_i & DSA = \text{on} \end{cases}$$

where $w_i$ is the calibration weight, which in this case may be set to 10 assuming both the cine acquisition and DSA factor functions will be included in the final factor multiplication. In addition, a simulation model may account for differences between dose rates for live subtraction roadmaps and normal live fluorography.

Once all parameters have been treated independently, the contributions from the individual dose rate factors may be multiplied together to give a "total dose rate" at a given point in time. Some dose rate factors may also be multiplied with the area of the beam cone at the IRP to give corresponding "KAP rate factors."

Based on the models and factor-dependent functions described above, the air kerma rate at the IRP and KAP rate may be calculated for any time point during the procedure. According to one embodiment of the invention, the current dose rates, such as current air kerma rate at the IRP and current KAP rate, may be summed throughout the course of the procedure to yield an accumulated air kerma at the IRP and an accumulated KAP. The total cumulative dose at any given time may be expressed as the sum of individual dose rates from the start of the procedure to the current time point, or:

$$d_{tot} = \sum_t d_t$$

The cumulative values may be kept as separate "fluoro" and "acquisition" parts until the end of the procedure for reporting and teaching purposes. The cumulative values could also be summed into a "total" IRP dose or KAP value at any point during the procedure and displayed to the user on the simulation display.

Tracking the cumulative air kerma at the IRP and the cumulative KAP rates over time enables the simulation to show how these rates change based on changes to operating settings, such as fluoroscopy, cine recording, or DSA acquisition.

The first time the current IRP dose and current KAP rates are calculated, they are set to the standard IRP dose and KAP rates calculated from step 502 above. In subsequent iterations, the IRP dose and KAP rates are calculated by generating a multiplication factor for all input parameters. Each generated multiplication factor is multiplied against the standard IRP dose and KAP rates.

Using the current IRP and KAP dose rates, a level of x-ray image noise and contrast may be calculated in step 505. The requested dose rate at the IRP can be calculated for a constant image quality (apart from the loss in image quality already mentioned above for the fluoro dose level and magnification). When this rate exceeds, e.g., the limits 22 mGy/min (low setting), 44 mGy/min (normal setting) or 88 mGy/min (high setting), the simulated noise may be increased. Based on empirical data, the relative noise should roughly double when the patient thickness increases by 6 cm over the threshold. Such an increase would be the same as increasing the requested dose 4-fold. Correspondingly, the relative increase in image noise may be calculated as:

$$n_t = \sqrt{\frac{d_t}{d_{threshold}}}$$

where $n_t$ is the noise multiplication factor, $d_t$ is the dose rate at time-step t, and $d_{threshold}$ is the applicable threshold dose rate.

The radiation simulation system may model the noise as standard white noise, shot noise, or similar additive noise common in the art of image processing. The noise multiplication factor may be applied to the white noise pattern to adjust the distribution of the white noise in the image. The adjusted white noise may then be applied to an x-ray image to simulate the effect of a noisy x-ray image.

In step 506, the surface area locations where radiation enters the patient may be calculated. The surface area locations may be determined using the three- or two-dimensional spatial models of the patient and beam emission models of the x-ray equipment. As described above, the patient model contains spatial information about the patient's anatomy, which may be for example a three-dimensional mesh grid. In one embodiment, a three-dimensional patient model may be obtained from segmented CT or MRI scans of the patient. Particularly, three-dimensional models of the skin may be used, since that is where the radiation enters the body and where incident doses are highest. Also, this is the most relevant canvas on which to visualize which parts of the patient have been irradiated.

Beam emission models are generated using information from the x-ray equipment model and operating settings above. The beam emission models characterize the geometry of the x-ray emission from the x-ray source. For example, the emission of x-ray beams may be modeled as having a tetrahedron (for flat panel detectors) or conical (for image intensifier detectors) shape, with its apex at the x-ray source and its base at the detector. The settings of collimators, wedge filters and FOV may also affect the resulting shape and intensity of the beam emission models. For example, collimator and/or FOV settings may restrict the base of a flat panel tetrahedron beam shape to a smaller rectangle, and wedge filters may cut off the corners of the tetrahedron base in a diagonal fashion to form an octagonal base on the tetrahedron. Also, the intensity distribution within the beam emission model may be modulated by the presence of wedge filters. The spatial coherence of the x-ray beams may be modeled by setting the base rectangle of the tetrahedron. Other geometric models may be used to characterize the shape of the beam emission, such as spherical, elliptical, square, rectangular, a polynomial function, or linear combination thereof. The shape and intensity of the beam cone may be modified depending on operating settings such as the use of collimators and/or wedge filters. In a biplane setting, several different beam emission models may be used simultaneously.

The surface area locations where radiation enters the patient may be determined by calculating the intersection between the spatial models of the patient and the spatial model of the beam emission.

Using the surface locations calculated in step 506, patient heatmaps may be generated in step 507. Patient heat maps for skin dose, absorbed dose and effective dose are calculated from combining information on dose rates, patient anatomy and patient geometry. In one embodiment, heat maps are stipple patterns, gray scales, or color scales applied to visual three or two-dimensional models of a patient's anatomy. The three-dimensional models may be, for example, mesh grid objects of the patient, and the two-dimensional models may be, for example, an outline of the patient's contour. The heatmap is generated by assigning a color scale for different values of dose rates. For example, red may be used to indicate high levels of IRP dose rates, and blue may be used to indicate low levels of IRP dose rates. The color scale is then applied across different locations of the patient's body, adding the color to the three or two-dimensional model that corresponds to the dose rate at that location of the patient's body. The heatmap may be dynamically updated and shown on the simulation display over the course of the procedure. In other embodiments, the heatmap may be used to display cumulative dose rates, displayed over the course of the procedure.

In one aspect of the invention, different heat maps may be used depending on the training objective. For example, a solid heat map may be used to display air kerma or skin dose rates, or corresponding cumulative doses, whereas a semi-transparent heat map may be used to show absorbed radiation inside the body, effective dose or estimated cancer risk per organ or body part.

In one embodiment of the invention, stochastic risk factors may be calculated in step 508. Using the dose rates calculated above, and the spatial information about the location of the patient's anatomical body parts, the effective dose at each body part can be estimated by applying a set of tissue or organ weighting factors to the dose rate. The effective dose at the body part can be used to estimate the stochastic and deterministic effects of radiation exposure.

The effective and entrance radiation doses received by the patient or a member of the operating team on a part of their body such as the skin, or their body as a whole, contribute to their increased risk of harm. Risks arising from deterministic effects, are effects that get gradually worse with the received dose, such as burns or hair loss. Risks stemming from stochastic effects are typically late-onset, and the severity of the effect is not related to the amount of received dose per se. An example of a risk arising from the stochastic effects of radiation is cancer.

In one embodiment, the accumulated radiation doses for the procedure may be compared to other stochastic radiation sources to enhance the user's understanding of the significance of the delivered dose. For example, the delivered dose rate may be compared to the equivalent number of chest x-rays or chest CT scans, or years of natural background radiation. In other embodiments, the risk of protracting cancer or dying as a result of the received dose during the procedure may be compared to the equivalent estimated life-time risks of death, cancer or injury from other activities. For example, the increased risk of dying from stochastic effects resulting from a dose of 25 mSV may be described to the user of the radiation protection simulator as being equivalent to the increased risk of dying from smoking 3500 cigarettes. These risk equivalents may or may not take into consideration individual risk factors such as age and gender, or lifestyle factors such as smoking, diet, or exercise habits, family and genetic history, or previous radiation exposure.

Deterministic effects appear predictably once a certain threshold dose has been exceeded, and the risk of the effect is related to the amount of delivered radiation. The simulation may therefore also monitor if any of these thresholds have been exceeded and, either immediately during the simulated procedure, or in a summative way afterwards, warn the user that an injury would likely have resulted had this been a real operation. Thresholds may be set to alarm users for risk of injuries such as, for example, erythemas, epilation, desquamation, ulceration, dermal necrosis, dermal atrophy, induration, telangiectasia, lens opacities and cataracts. These dose rate thresholds may be used to trigger displays of images of the typical injuries that occur after exceeding the thresholds, or when in time the onset of the injury can be expected to occur.

In one aspect of the invention, the stochastic risk factors may be applied to the heatmap to generate a map visualizing the estimated increased cancer risk caused by the current operating settings.

In step 509 a current three-dimensional scatter radiation profile may be calculated to model the secondary radiation that is scattered back from the patient and onto an individual from the medical team in the operating room. The scatter radiation profile is based on information about patient anatomy, patient dose rates at different points in time, and the x-ray beam emission geometry.

In one embodiment, the model may be built on regions at different distances from the central beam, where the boundary of each region corresponds to a certain isosurface with a fixed scattering dose rate. The isosurfaces may be chosen as locations where dose rates have predetermined values. For example, the isosurfaces may be chosen as locations where dose rates are 4.0, 2.0, 1.0 and 0.5 mGy/hr. Based on studies that suggest scatter dose rate is approximately proportional to the KAP rate at a set distance and scattering angle, the scatter radiation profile may model the dose rates at the isosurfaces to be proportional to changes in KAP rate.

In a preferred embodiment, the scatter radiation profile may model the scatter radiation isosurfaces as uniform around the central beam axis between the x-ray tube and detector. The scatter radiation profile may also preferably be parameterized by a one-dimensional function, expressing the radius of the isosurface at a given point along the central axis as a function of distance from the x-ray tube. The function may be, for example, a polynomial function, a linear combination of semi-circular shapes, a Bezier curve, or as a magnetic dipole function. In other embodiments, the isosurfaces may be modeled to have elliptical shapes around the central beam, by using separate short radius and long radius profile functions to determine the constant dose rate ellipse in a certain plane perpendicular to the central beam.

In one embodiment, the isosurface may be modeled as a three-dimensional surface. A three-dimensional model may be used with spatial data about the x-ray equipment and operating room, such as for example, information about a real system installed in a hospital setting or when such detailed data is available from the vendor of the specific x-ray system.

In one aspect of the invention, the scatter radiation profile may model x-ray shielding objects that may be present in an operating room, such as the patient table, the x-ray tube and detector, the bodies of the operator or team themselves, or dedicated radiation protections shields. The scatter radiation profile may reduce the scatter radiation where there is a presence of shielding objects.

In step 510, the amount of current scatter radiation is calculated by applying the current KAP rate to the scatter radiation profile. Once the scatter radiation profile around the central beam and all the corresponding scatter radiation isosurfaces have been determined, these can then be used to calculate, for any given time point, the scattered dose rate for any point in space around the patient. More specifically, this can done by selecting the highest dose rate isosurface, for which the point in space is located inside said isosurface. The dose rate of the specific point in space may then be set to the same dose rate as the selected isosurface. Alternatively, the dose rate of the specific point in space may also be calculated using a linear combination of the scatter dose rates for the two isosurfaces closest to the point, where the dose rates are weighted together based on the point's distance to each isosurface.

As the angulation of the c-arm and other x-ray equipment model parameters change, the scatter field and three-dimensional scatter isosurfaces will change accordingly. In the case of the c-arm angulation, rotated isosurfaces may be computed using the application of a three-dimensional rotation matrix. The effect of all other input parameters may be accounted for by multiplying the initial scatter dose rate of each scatter isosurface with the KAP rate factor computed by the radiation metrics processor, since the KAP is approximately proportional to the scatter dose.

In one embodiment, the cumulative scatter radiation around the patient may be calculated over time. This is accomplished by dividing the space around the patient in the operating room into sub-volumes, as described in more detail with reference to FIGS. 9A-D. For each boxed sub-volume in space around the operating table, the current scatter dose rate is calculated and summed over time per sub-volume.

In one embodiment of the invention, two-dimensional cross-sections of isocurves for scatter may be calculated in a step 511. The calculations are based on the three-dimensional profiles described above. The cross-section may be derived using the position of a medical team member in relation to the position of the c-arm. For example, a typical position for a physician in an operating room performing an endovascular procedure with a right femoral approach, is on the patient's right side and to the right of the c-arm, at about a 45 degree angle from the c-arm plane. A cross-section for the physician could be based on this position and angle.

In step 512, dose values at specific locations of the medical team member's body may be calculated. Using either the two-dimensional or three-dimensional scatter radiation profiles described above, and information about the team member's position, the scattered radiation dose at the precise team member's location may be determined. Further, spatial information about a team member's anatomy can be used to determine the precise location of specific points-of-interest that include radiosensitive organs, such as hands, eyes, thyroid gland or gonads. Modeling the team member's anatomy in a similar manner as the patient anatomy described above, enables the radiation metrics processor to determine the positions of different organs or body parts based on the individual's real height and composition. For example, the specific point in the scatter field representing a physician's eye dose may be set based on the individual's real eye level; a higher point would be chosen for a tall physician and a lower point for a short physician.

In one aspect of the invention, the position of the operating physician, team, and specific points on their bodies, such as e.g. eyes, thyroid glands, hands and gonads, may also be tracked during the procedure, by equipping them with positional sensors. The scatter radiation dose rate may be updated to correspond to the scatter radiation profile at the new location. In this way, the scatter radiation profile enables the simulation to dynamically account for changes in position as team members move around in an operating room. This allows the simulation to account for how well the team reacts to radiation events, such as for example, if the team steps away from the machine when radiation is activated, or moves hands out of the x-ray beam.

In step 513, the metrics associated with the current point in time are saved into a timeline. Over the course of an entire procedure, the timeline will contain metrics at different points in time which can be used to visualize the relationship between a set of control input parameters and dose rate over time. In one embodiment the radiation metrics calculated at each point in time, are associated with the point in time they were calculated during the procedure. Each time the radiation metrics are updated, they may then be stored in, for example, a data collection storage. The storage of radiation metrics across different points in time may then be used to visualize dose metrics as curves that are a function of time. Because one of the biggest dose contributions to a patient or team member may occur over a limited time frame of the procedure, it is useful for the user to comprehend how the radiation metrics varied at any point in time, if they used the x-ray equipment in an efficient way, and how different doses changed as a result thereof.

In step 514, performance evaluations may be generated based on the timeline metrics calculated in step 513. Performance evaluations may be provided to users of the simulation, describing how well their radiation dose management for the procedure was performed. The performance may be evaluated against different standards, such as for example, the performance of others in the hospital, nation, or globally. The evaluation may be based on a comparison of the reached simulated dose levels for a user of the radiation simulator to measured average values for the same procedure within the same catheterization lab, same hospital, region, country, or globally. Such average dose values can be obtained from hospital quality systems, or in national or global databases and surveys. The dose values may also be compared to other metrics, such as for example, a median dose or a range of doses like a confidence interval or quartile. The performance may also be evaluated against the user's own past performance, hospital and society standards and guidelines, or estimated healthcare cost to society or the hospital. The system may further allow the comparison values to be freely configured by the user, to allow the radiation simulator to compare with values from the hospital or country in which it is placed.

In one embodiment of the invention, the simulation system may include a step of calibrating 515. The step of calibrating may include generating a calibration weight that, when applied to the output radiation metrics, produces radiation metric values that are closer to approximating the x-ray equipment and patient models. For example, the output radiation metrics may be calibrated or scaled to approximate the x-ray equipment used in a real cath lab. In one embodiment, the calibration weights may be calculated by using radiation metrics generated during a real x-ray guided procedure. The ratio of the real radiation metrics to simulated radiation metrics may then be used to determine a calibration weight. In this way, the calibration weights allow the simulation to estimate how large an effect of implementing a simulator training program would have on the actual radiation quality metrics within a hospital. The calibration weight scales the output radiation metrics in a similar fashion as the calibration weights that scale the factor functions described above.

In another aspect of the invention, the system may compare the user's obtained simulated dose levels to a standardized or recommended threshold level. Hospitals often have their own thresholds based on local quality standards, and exceeding the thresholds may result in certain actions to be taken or costs to be incurred. Such actions may include booking a follow-up visit for a patient who has received a high dose, sending ALARA warning letters to personnel who have exceeded a local ALARA dose threshold, or suspending personnel who have exceeded maximum dose levels as regulated by law. Such thresholds are typically found in hospital radiation safety handbooks and manuals, or published by societies and regulatory authorities. The thresholds in the present invention may be configured to correspond to the local laws, recommendations and guidelines where the simulation is placed.

In one aspect of the invention, the simulation may use the performance evaluation and record of threshold violations to estimate how poor performance impacts costs on health care facilities or providers. Generally, a hospital incurs costs for issuing ALARA warning letters, additional follow-up patient visits, or suspending personnel. If the performance evaluation indicates that ALARA warning letters were issued, follow-up patient visits were scheduled, or personnel was suspended, the hospital may use that information to estimate the expected cost it would incur. In another aspect of the invention, the estimated costs to society may be calculated using an associated cost per man-Sievert or person-Sievert of exposure. Such costs, or ranges of costs, can be obtained from public health and safety studies.

In one aspect of the invention, the simulation may simulate any number of x-ray machines. Multiple x-ray machines may be simulated by simulating the effects of each machine separately, and then combining the net effect of each machine. Thus, for example, in a biplane configuration which consists of two x-ray machines machine A and machine B, the steps described in 501-513 may be performed independently for each machine to generate two sets of IRP and KAP dose rates. The net effect of each machine on the patient and medical team may then be calculated by combining metrics associated with each machine. The total effect of any number of additional machines may be calculated by likewise combining the IRP and KAP dose rates of each additional machine.

Figure 6B:
FIGS. 6A and 6B illustrate how x-ray fluoroscopy noise and contrast level may change as the user changes the control input parameters according to one embodiment of the invention.
Figure 6A:
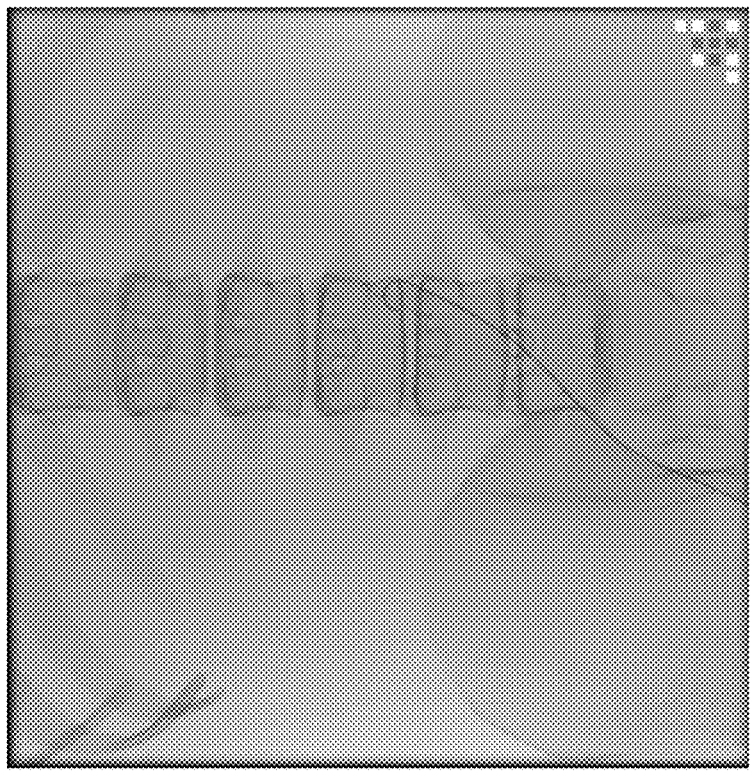

FIG. 6 is an example of how x-ray fluoroscopy noise and contrast level may change as the user changes the x-ray equipment model control parameters. In FIG. 6A a situation is depicted where the radiation dose level is such that the x-ray image quality is very good and the inserted wire is clearly visible. However, this high image quality results in a high radiation dose to the patient and the operating team.

In FIG. 6B the opposite situation is depicted. Here the radiation dose is kept very low, but because of that the wire is barely visible which may risk negatively influencing the successful execution of the medical procedure. An optimal use of radiation balances these two extremes and depends on the operator's procedural and radiation reduction skills.

Figure 7:
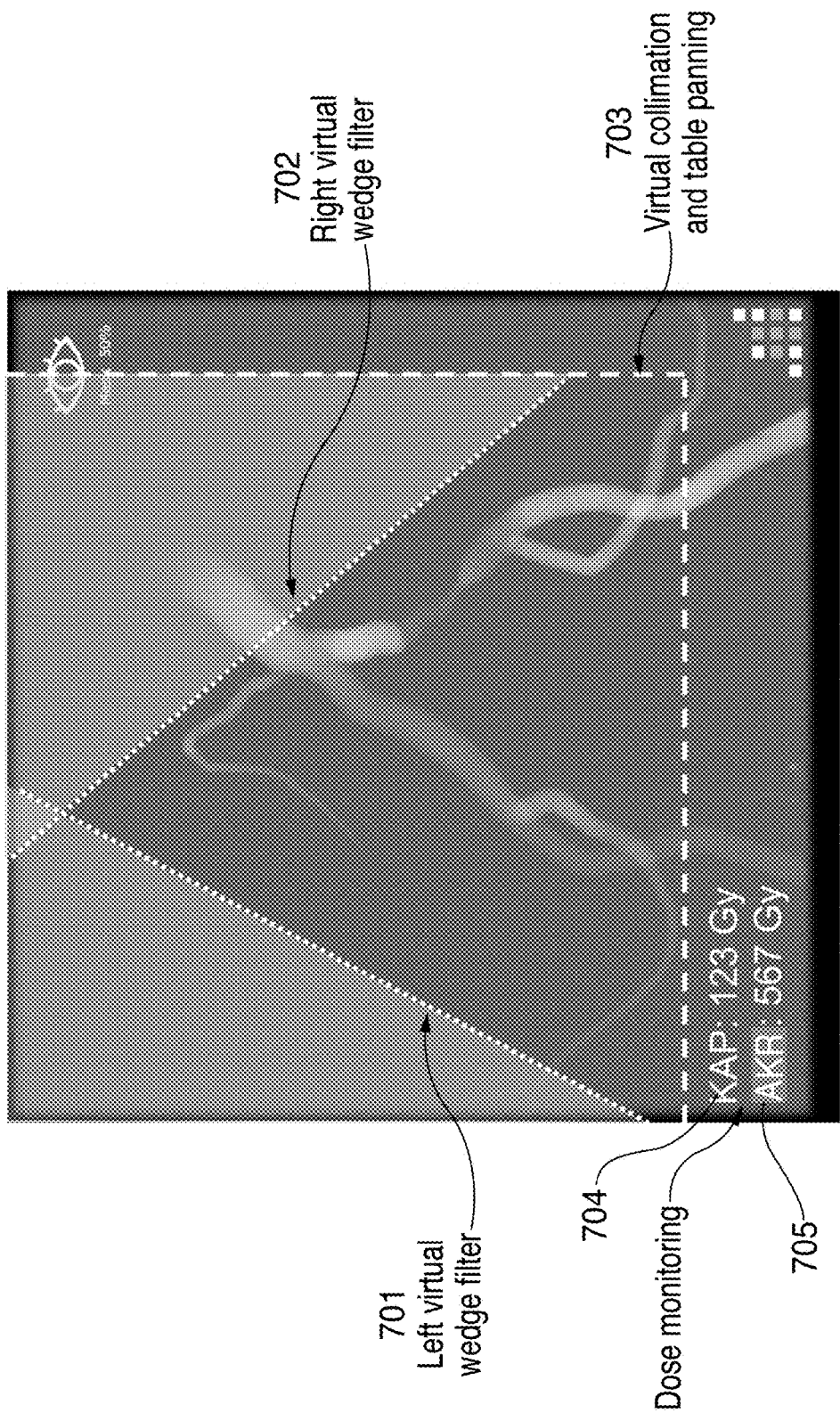
FIG. 7 illustrates how virtual collimators, wedge filters and table panning indicators may be shown on the x-ray imaging simulator according to one embodiment of the invention.

FIG. 7 shows another embodiment of the invention that simulates the effect of operating settings on the x-ray image. Specifically, FIG. 7 uses virtual indicators to show the effect of collimation, wedge filters, and table panning on the simulated x-ray image. Virtual indicators may be used as a means of positioning collimators, wedge filters, and the patient table. These indicators are overlaid on the x-ray image and make it possible to position the parts of the equipment without having to use live x-ray. The virtual collimator and table panning indicator 703, may be rectangular or circular, may be overlaid as a dashed line on the last captured x-ray image on the screen. Virtual collimator and table panning indicator 703 shows which part of the full x-ray view will be visible once the live x-ray is turned on. Virtual collimator and table panning indicator 703 may also be used to show that if the table is moved, the dashed lines may move correspondingly to show which part of the patient will be visible once live x-ray is activated. Left virtual wedge filter indicator 701 and right virtual wedge filter indicator 702 may also be shown on the x-ray imaging simulator screen as dotted lines to indicate their new position. Optionally, the area under the virtual collimators and/or wedge filters may be shaded to visualize how the image will change when they are in their new positions.

In FIG. 7, the display also enables the user to visually monitor the radiation metrics that the radiation metric processor is calculating. As shown in FIG. 7, these metrics 704-705 may include the air kerma at the IRP and KAP values calculated by the radiation metrics processor. These metrics may be visualized on the display of the simulator during any part of the simulation. When operating setting or input parameters change, the metrics may be dynamically updated. The display may show current metrics, accumulated metrics, or both.

FIGS. 8A, B and C show embodiments where radiation dose heat maps can be overlaid on the patient's anatomy model in three dimensions. The image of the patient model may further be overlaid with distinct markers to show different types of information. For example, distinct markers 801-803 in FIG. 8A may be used to show the locations and levels of peak skin dose, or the projected outline of the x-ray beam intersection with the skin. They may also show the estimated increased cancer risk and/or effective dose per organ or part of body, given the available data.

In one aspect of the invention, the display may show the beam emission model described above. For example, if the beam emission geometry is modeled as a tetrahedron, the display may show a tetrahedron 807 as shown in FIG. 8B (and as 804 in 8C) with its apex 805 at the radiation source, and intersecting the patient at 806. The shape and intensity of the beam can also be cut or modified to include effects of collimators and/or wedge filters. In figures the 8A-8C the fluoroscopy beam tetrahedron is visualized to help the user understand where on the body the patient is currently being exposed.

FIG. 8A shows an oblique front view of the patient. The radiation exposure on the chest and abdomen is indicated by the vertical stipple pattern shown on the skin in the area 803. In this embodiment, the vertical stipple pattern indicates a low level of exposure. FIG. 8B shows a left side view of the patient. The radiation exposure on the patient's back is indicated as horizontal stipple patterns, which in this embodiment indicates high dose exposure levels. FIG. 8C shows an oblique back view of the patient. The top region of the patient's back that has received high radiation exposure as indicated by the horizontal stipple pattern. The radiation exposure is higher on the patient's back than the patient's front, since the beam source is closer to the patient's back.

FIGS. 9A, B, C and D exemplify how the three-dimensional spatial sub-volume boxes are used to calculate the scatter radiation dose distribution in each box. FIGS. 9A-D illustrate two-dimensional slices of scatter radiation isosurfaces 901-904. The scatter radiation isosurfaces 901-904 are between a C-arm source and detector. The operating room may be subdivided into multiple subvolumes. For example, in FIGS. 9A-D one particular subvolume A is indicated by boxes 905 and 907, and a different subvolume B is indicated by boxes 906 and 908. Any subvolume located in the scatter radiation isosurfaces 901-904 indicate a subvolume that is exposed to a scatter dose rate from that isosurface. During computation of the whole current scatter field dose rate, several such scatter dose rate isosurfaces with different magnitudes will be calculated and added to each subvolume when the subvolume is inside the highest dose isosurface.

In FIGS. 9A and B, a side and a head view of the patient are shown, respectively, where the x-ray fluoroscopy unit is positioned in anterior-posterior angulation. FIGS. 9C and D show a different situation at a different time point of the procedure, where the angulation of the x-ray fluoroscopy unit has been changed to an oblique view. FIG. 9C shows that subvolume A, as indicated by box 907, is no longer inside the scatter radiation isosurface 903, indicating that it no longer receives a dose rate contribution from that isosurface. In contrast, the subvolume 908 in FIG. 9D still receives a dose rate contribution from isosurface 904. As the procedure progresses, the accumulated scatter radiation dose rates per subvolume continue to be summed over time. In the embodiment shown in FIGS. 9A-D, subvolume A (indicated by boxes 905 and 907) would have received a lower total scatter dose than subvolume B (indicated by boxes 906 and 908) by the end of the procedure.

Using the methods disclosed above, a three-dimensional volumetric estimation of the instantaneous and cumulative scatter fields around the patient, with a given spatial resolution, can be obtained. These scatter fields may then be visualized in various ways, to create the best possible learning experience for the user of the system. In one embodiment, the volumetric scatter field may be visualized in three dimensions as a number of semi-transparent isosurfaces of different colors around the patient table, where the color may depend on the dose rate or cumulative dose at each isosurface. Such a visual representation may also be rotated by the user to see the scatter situation from any angle.

Alternatively, specific cross-sections of the scatter field may be visualized, as they may be easier for the user to understand than the complete scatter field. One such cross-section of particular interest is where the scatter field intersects the body of a member of the operating team located close to the patient. Typically, the closer a member of the operating team is to the patient, the higher occupational scatter dose they will receive, and the most interesting cross-section of all is therefore that of the operating physician, who will normally receive the highest dose.

FIGS. 10A and B are cross-section visualizations of sets of two-dimensional scatter radiation isocurves around the operating surgeon according to another embodiment of the invention. Each isocurve 1001-1004 represents a different scatter radiation level. FIG. 10A shows a head view, where the scatter radiation at different heights throughout the operator's body can be viewed. FIG. 10B shows a top view with the C-arm in a lateral angulation, where the scatter field surrounding the patient table can be viewed.

Figure 11B:
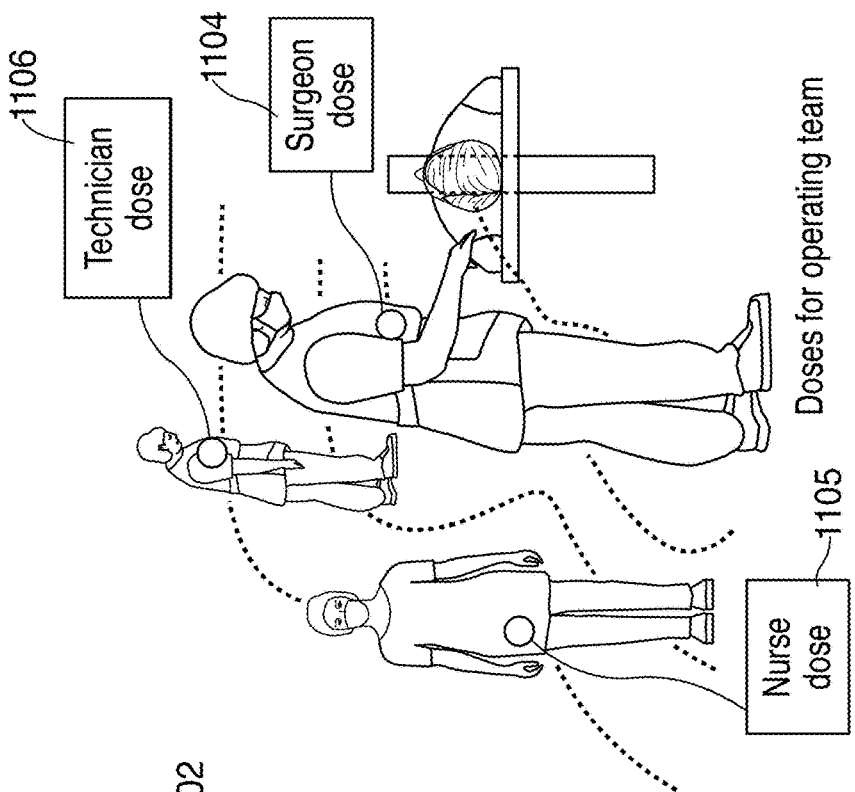
FIGS. 11A and B show scatter radiation visualizations according to another embodiment of the invention.
Figure 11A:
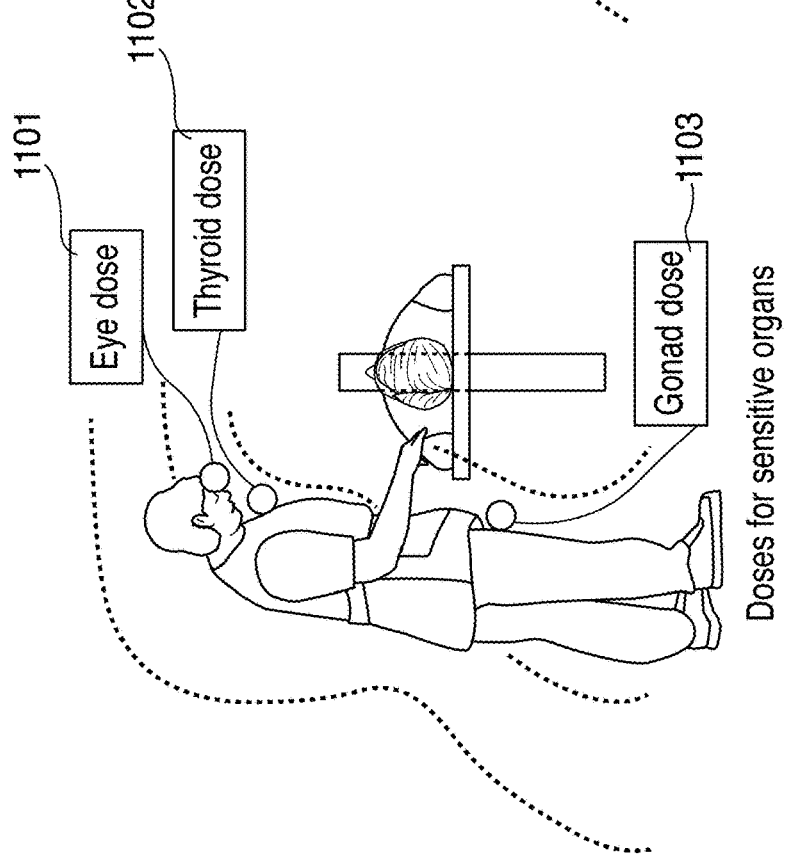

FIGS. 11A and B illustrate the use of isocurves to determine how fixed or moving medical team members are affected by scatter radiation. In FIG. 11A, positions corresponding to radiation sensitive parts of the physician's body such as the eyes 1101, thyroid gland 1102, and gonads 1103 are used to view dose rates at those locations. As described above, scatter radiation dose rates at these locations may then be used to determine stochastic or deterministic risks for those particular organs. In FIG. 11B, the positions of multiple team members 1104-1106 are used to compute compound dose estimates for each individual. Using motion tracking or position sensor technology, these estimates may also change over time and may be used to include benefits from radiation reduction techniques such as stepping back from the table when fluoroscopy is active.

The dose rates and cumulative dose measurements at the different points-of-interest and for the different operating team members may be presented together on a display. These values may also be multiplied by one or more attenuation factors, which the user of the radiation simulator can toggle on and off, corresponding to a reduced dose resulting from use of different radiation protection equipment such as, for example, protective shields, aprons, glasses, neck collars, gloves, or head covers. A display interface may also consolidate both patient-, operator- and team-related dose information from both primary and secondary radiation, in a compound overview format, making it easy for the trainee to quickly get a picture of the risk level in a certain radiative situation.

Figure 12:
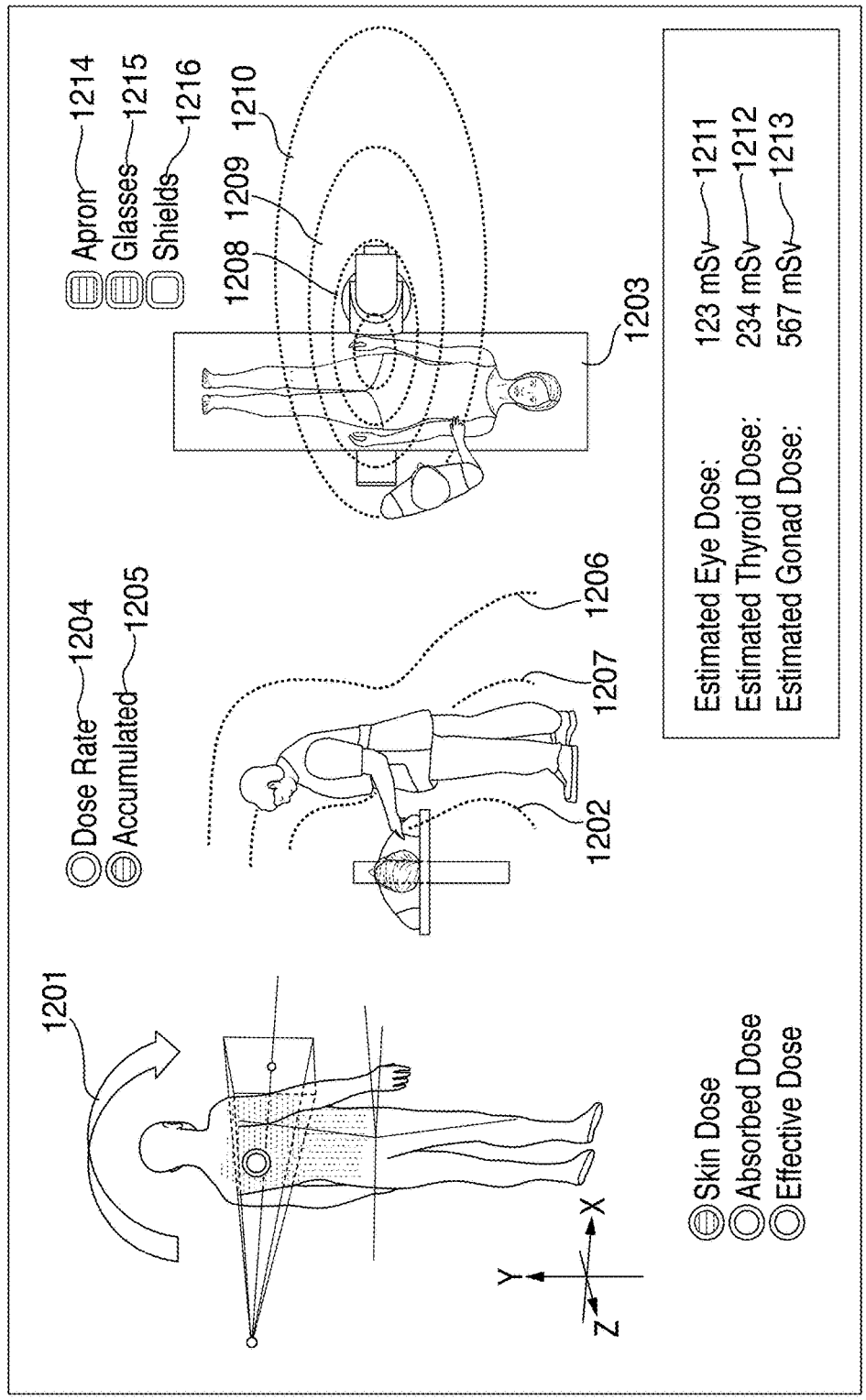
FIG. 12 illustrates a display interface to present both patient-related and scatter-related dose according to one embodiment of the invention.

FIG. 12 illustrates a display for showing radiation metrics and dose heatmaps according to one embodiment of the invention. The display may show patient-related dose information 1201 and scatter-related dose information 1202 and 1203 to the user of the simulation system. The user may choose whether to display the current dose rate measurements 1204 or the total accumulated doses 1205. A dynamically updated rotatable three-dimensional model of the patient 1201 shows either actual skin dose (or dose rate), absorbed dose or effective dose (which is related to the increased cancer risk). Scatter isocurves 1206-1210 show the radiation field around the operating physician and patient table. The operator eye 1211, thyroid 1212 and gonad 1213 doses are calculated and displayed, and effects on these values from using radioprotective equipment such as lead aprons 1214, glasses 1215 or shields 1216 are also interactively presented to the user in order to improve the training.

Figure 13:
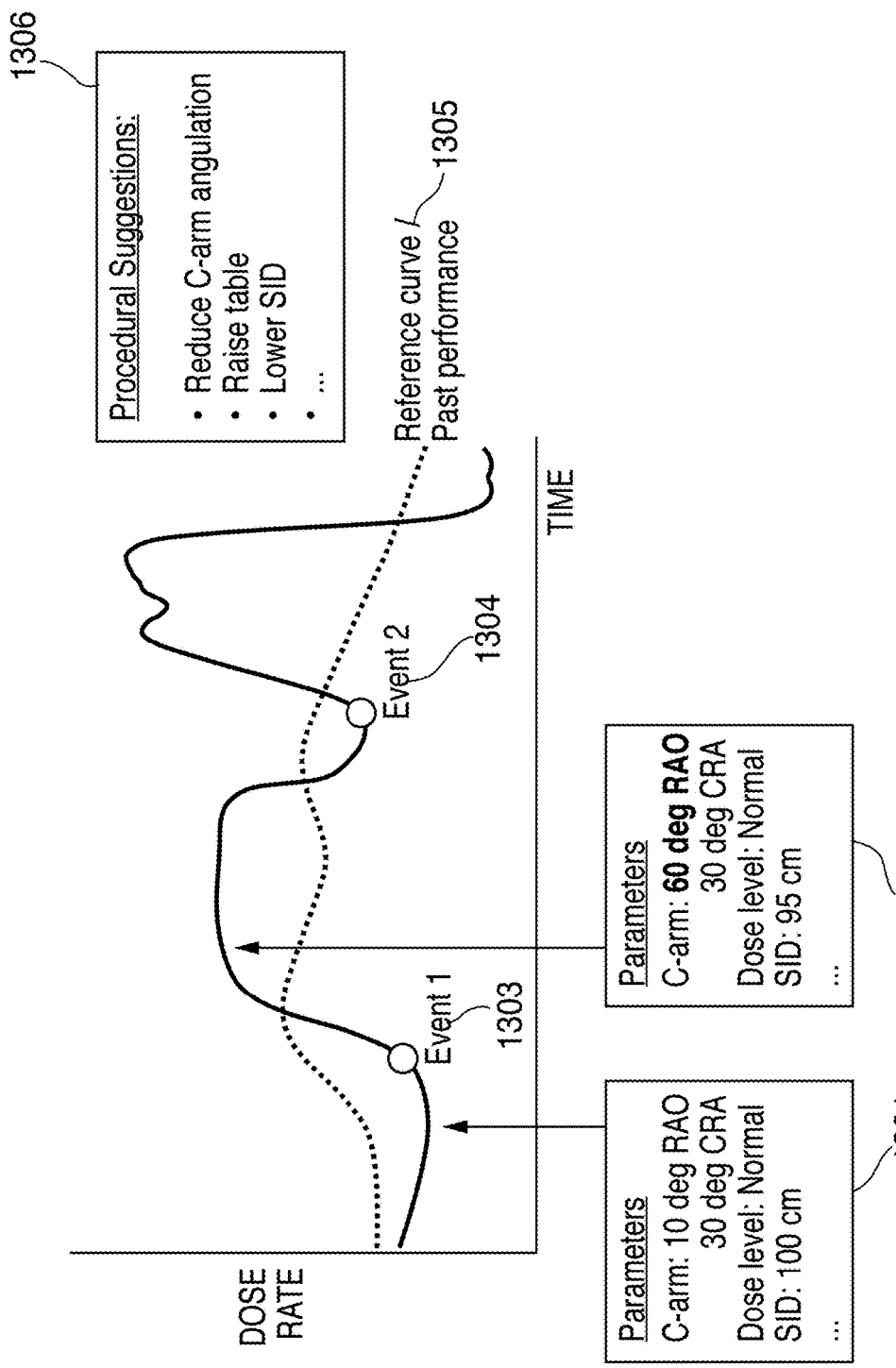
FIG. 13 is a timeline of radiation metrics according to one embodiment of the invention.

FIG. 13 shows one embodiment comprising a timeline of the procedure and a corresponding dose curve, where the amount of radiation is plotted against time. The graph can show either dose rate at the IRP, skin dose rate, KAP rate or any other radiation metric calculated by the radiometric processor. As the procedure progresses and the operator changes the x-ray equipment model control inputs, the resulting dose rate will go up and down. By clicking on or hovering over a time point on the curve, the user can easily access windows 1301 and 1302 shown next to the timeline showing what the control input parameters were at that point in time, allowing the user to understand why the dose was high or low at any given time. Control input changes that have caused large increases in dose rate over a short timeframe can be highlighted, which is shown for the C-arm angulation in the figure. Also, events 1303 and 1304 which have caused large increases in dose rate can be identified automatically and indicated on the curve as shown. One or more additional curves 1305 showing reference or past performance curves can also be shown in the graph to allow the user to compare their performance to a set standard or see how their skills are improving with training. Furthermore, by using known information about a certain type of procedure, and/or comparing to a reference dose rate curve, specific skills where the user's radiation reduction techniques are weak can be identified and a list of possible procedural improvements 1306 that they should focus on in their continued training can be suggested.

The automatic annotations of events may be made for example at the local maxima, minima, or inflexion points of the metric curve, or at points on the timeline where large increases have occurred. They may also be determined by comparisons of curves to standard reference curves, where points exceeding the reference curve by a certain degree would be marked. Events may also be annotated by identifying time points where equipment parameters could have been optimized, such as for example, when the fluoroscopy pedal has been pressed for a long time without any movement of the surgical instruments.

The automatically identified events may subsequently be used to assess if desired dose reduction techniques were used or not, and to give recommendations to the user on how they could have further reduced radiation. This may, for example include suggestions of appropriate usage of shutters and wedge filters, reduction of unnecessary fluoroscopy time, less use of cine acquisitions, changing table position or C-arm angulations more often.

Figure 14A:
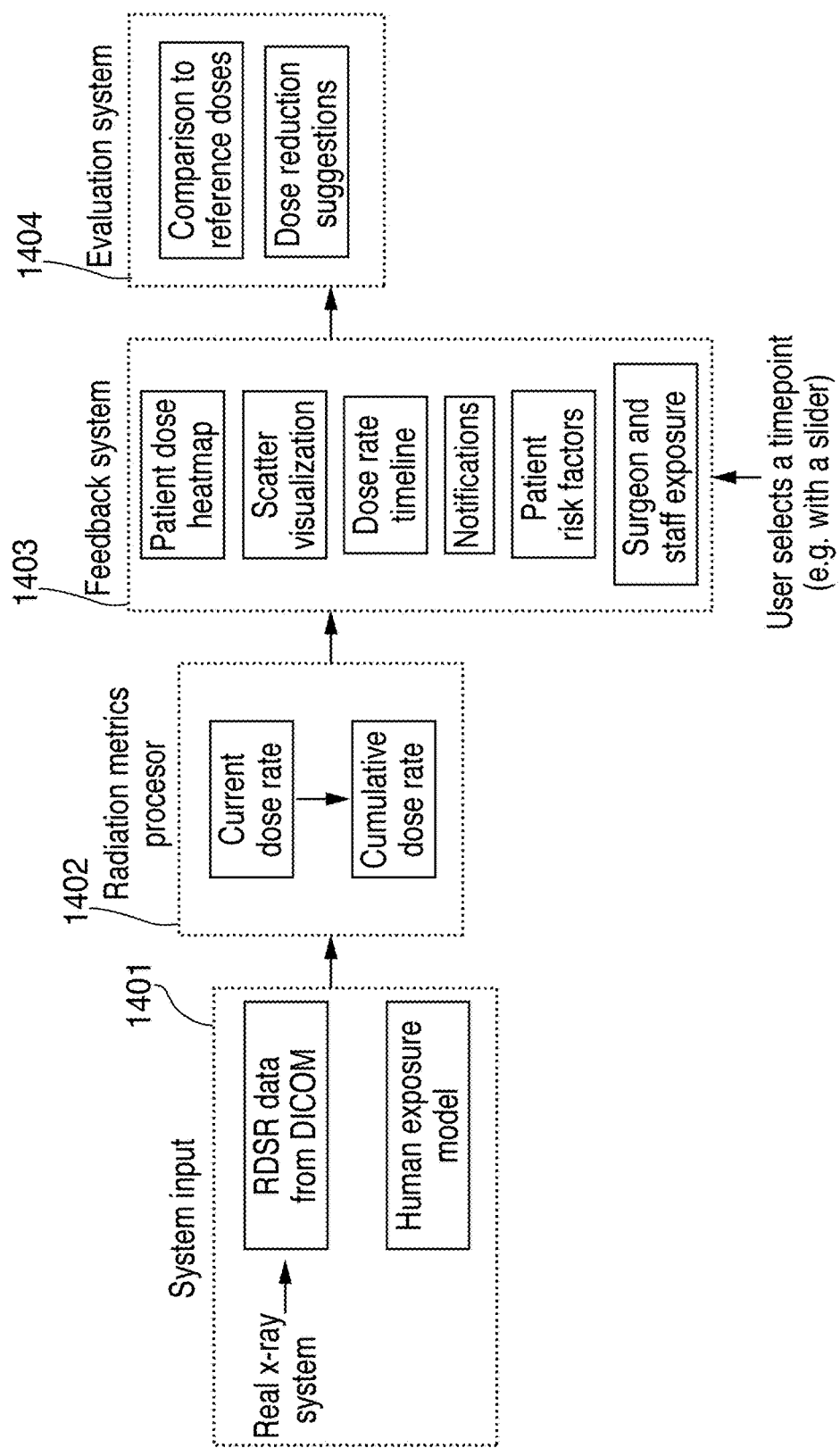
FIGS. 14A and B shows recorded data being used as system input to the simulation according to one embodiment of the invention.

FIGS. 14A and B show that in one aspect of the invention, recorded data on parameters and radiation metrics from a real procedure may be used as input for the x-ray equipment models and patient models. In this way, the simulation may be executed to reflect how real x-ray equipment would operate on actual patients. The recorded data may be DICOM formatted data, collected as radiation dose structured report (RDSR) records. An example of an RDSR is shown in FIG. 14B. As shown in FIG. 14A, the system input is provided by the RDSR data instead of from an input interface controlled by the user. Thus, the different parameter values at each moment in time recorded on the RDSR may be used as input to the simulation.

In one embodiment where system input is processed from an RDSR, the simulation may provide the user with an interface that allows the user to step forward or backward in the time of the operation. For example, the interface may be a slider, where the user may move forward and backward in time in the procedure, and the radiation metrics, visualization and feedback/evaluation at each moment may be displayed at the moment of time corresponding to the position of the slider.

Figure 15:
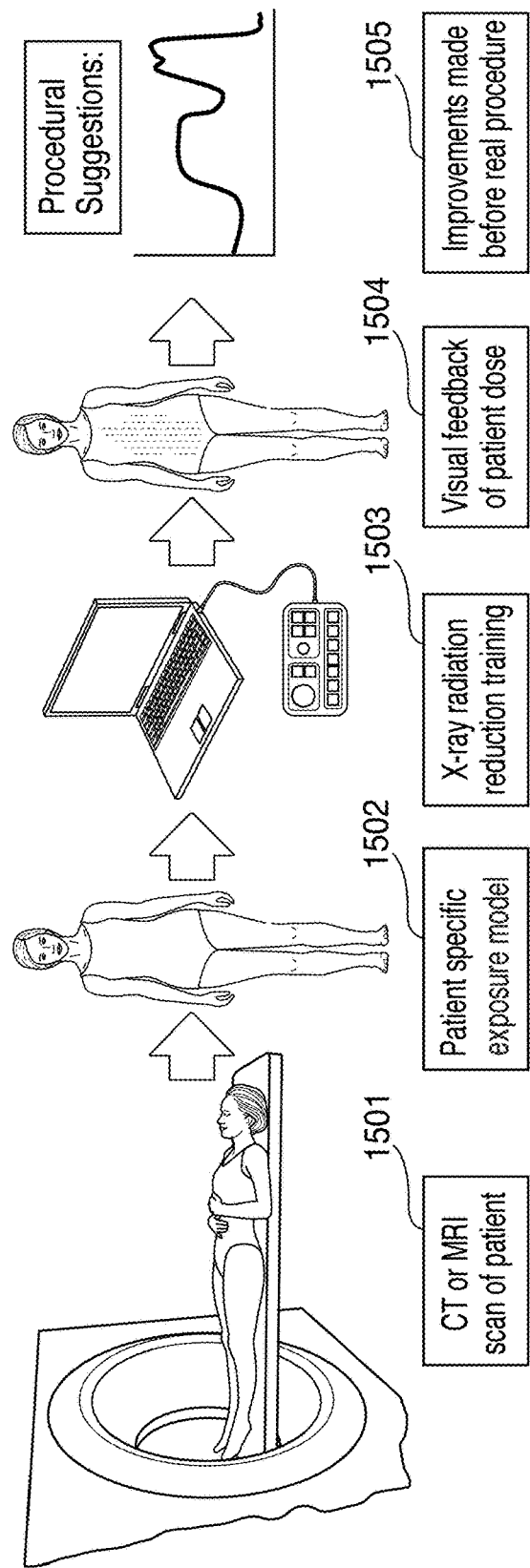
FIG. 15 illustrates the use of the invention for patient-specific training according to one embodiment of the invention.

FIG. 15 shows one embodiment of the invention where the human exposure model is based on a patient-specific anatomy. A CT or MRI scan is rendered in 1501. The scan may be of the patient or medical team member. The scan may then be segmented to determine the locations of different human anatomies and create a human exposure model 1502. These locations may then be used to create a three-dimensional mesh model, which may include the structure and location of human organs. For example, the human exposure model may include the size and shape of the heart, brain, eyes, thyroid and gonads. With this patient-specific model, the user may run a simulated x-ray guided procedure and work on radiation reduction training 1503. The simulation system may then provide feedback 1504 and performance evaluations 1505 as described above. In this way, the patient-specific model can be used to simulate a real procedure, enabling the medical professional or team to practice how to best minimize the radiation for the particular patient in a safe and radiation-free environment. The visual feedback on expected radiation to the patient body and suggestions on procedural improvements during the practice run can then be used to minimize the actual radiation delivered to the patient during a real procedure.

Figure 16B:
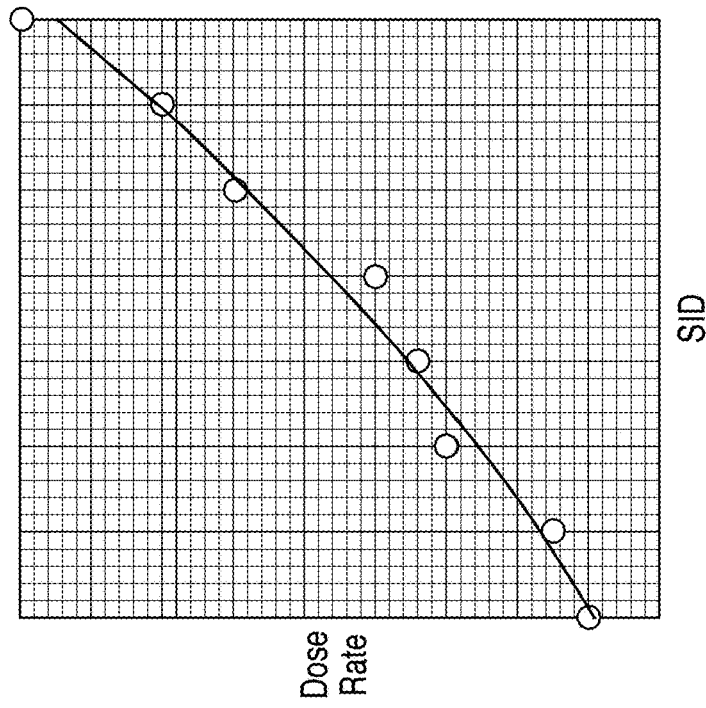
FIGS. 16A and B show the process of calibrating the invention to an individual piece of x-ray equipment according to one embodiment of the invention.
Figure 16A:
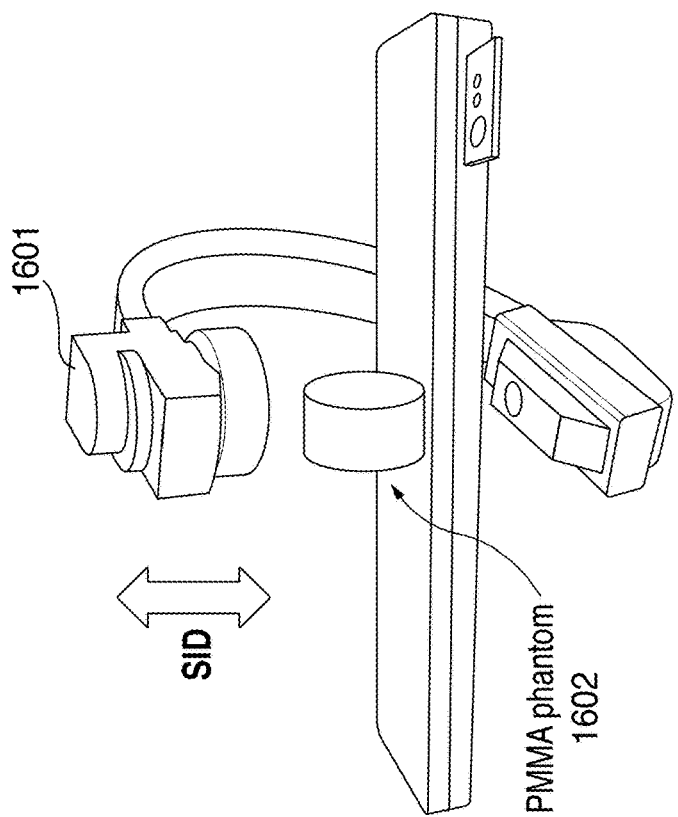

FIGS. 16A and B show that in one aspect of the invention, the simulation system may be calibrated to a piece of x-ray equipment by applying a calibration weight to scale the output radiation metrics. The calibration weight scales the output radiation metrics in a similar fashion as the calibration weights that scale the factor functions described above. For example, the output radiation metrics may be calibrated or scaled to approximate a real cath lab for which training is to take place. The calibration weights allow the simulation to estimate how large an effect of implementing a simulator training program would have on the actual radiation quality metrics within a hospital.

Calibration weights may be generated by placing one or more standard radiation "phantoms", a type of block made from PMMA (poly-methyl methacrylate) and frequently used as a dosimetry analogue to human tissue, on the operating table and measuring how the radiation metrics change across each parameter. FIG. 16A shows an example of a calibration weights being generated for the SID parameter. An image detector 1601 is moved up and down in fixed steps, thereby changing the source-image-distance (SID) and corresponding dose rate for a certain SID. The radiation dose at the PMMA phantom 1602 is measured at each SID. FIG. 16B shows the obtained dose rate data points plotted against the fixed SID settings and a best fit of the curve. The defining values of the best fit parameter model can then be fed into the simulated radiation metric algorithms as calibration weights, allowing the calculated dose rates during use of the present invention to better correspond to the values of the individual piece of x-ray equipment. Alternatively, the same calibration procedure can be used as a means to first determine which type of factor function, such as linear, quadratic, exponential, or logarithmic, would best model the specific x-ray system and then used to optimally fit the chosen factor function to the measured curve.

The systems and methods described above can be used to teach radiation reduction techniques for various types of x-ray or fluoroscopy guided procedures, including but not limited to endovascular and/or percutaneous applications, trauma surgery, embolization, orthopedic surgery, investigations of the gastrointestinal tract, placement of CVC and PICC lines, placement of feeding tubes, urological surgery, oncology applications, biliary drainage and discography.

The systems and methods described above are particularly suited for simulating endovascular surgery. An endovascular procedure is a minimally invasive, image guided procedure that uses medical instruments which are introduced into the blood vessels of the patient through an opening, typically in the groin, wrist or neck area, and their motion inside the body of the patient is visualized by the fluoroscope or x-ray system. It is therefore most useful for procedures within the fields of interventional cardiology, interventional radiology, vascular surgery, interventional neuroradiology, electrophysiology, structural heart disease, interventional oncology and cardiovascular surgery.

Variations, modifications, and other implementations of what is described herein may occur to those of ordinary skill in the art without departing from the spirit and scope of the present invention and its claims.

The invention claimed is:

1. A system for determining an amount of radiation exposure to one or more humans during a simulated x-ray guided medical procedure without exposing a human to ionizing radiation, the system comprising:
   an x-ray equipment model that simulates emission of radiation from x-ray equipment during the simulated x-ray guided medical procedure without emitting ionizing radiation, the x-ray equipment model comprising a first set of input parameters corresponding to operating settings controlled during the simulated x-ray guided medical procedure, wherein the first set of input parameters are configured to vary during the simulated x-ray guided medical procedure;
   a human exposure model that simulates one or more human anatomies during the simulated x-ray guided medical procedure, the human exposure model comprising a second set of input parameters corresponding to a location and structure of one or more human anatomies during the simulated x-ray guided medical procedure;
   a radiation metric processor that calculates at least one radiation exposure metric to the one or more humans located in a room of the simulated x-ray guided medical procedure, wherein the calculation of the radiation exposure metric occurs during the simulated x-ray guided medical procedure, and is based on the first set and second set of input parameters and a model that associates a change in the first set and second set of input parameters with a change in the radiation exposure metric; and
   a feedback system for outputting information based on the at least one radiation exposure metric during the simulated x-ray guided medical procedure
   wherein the model that associates the change in the first set and second set of input parameters with the change in the radiation exposure metric calculates a current dose rate $d_t$.

2. The system according to claim 1, wherein the simulated x-ray guided medical procedure utilizes simulated x-rays to visualize the one or more human anatomies without delivering x-rays to the one or more humans.

3. The system according to claim 1, wherein the current dose rate $d_t$ is calculated based on a base dose rate $k_{ref}$ and a multiplication factor $f_i(w_i,p_t)$, the multiplication factor is based on a weight $w_i$ and a value of an input parameter $p_t$ from the first set or second set of input parameters.

4. The system according to claim 3, wherein the current dose rate $d_t$ is calculated based on the product of each multiplication factor $f_i(w_i,p_t)$ for each of the first set and second set of input parameters $p_t$, and the base dose rate $k_{ref}$.

5. The system according to claim 4, wherein the radiation metric processor calculates a new current dose rate $d_t$ based on a change to the x-ray equipment model during the simulated x-ray guided medical procedure, and the change to the x-ray equipment model corresponds to a new input parameter value from the first set of input parameters.

6. The system according to claim 4, wherein the second set of input parameters of the human exposure model may be varied by an operator during the simulated x-ray guided medical procedure.

7. The system according to claim 6, wherein the radiation metric processor calculates a new current dose rate $d_t$ based on a change to the human exposure model, and the change to the human exposure model corresponds to a new input parameter value from the second set of input parameters during the simulated x-ray guided medical procedure.

8. The system according to claim 4, wherein the radiation metric processor receives a new input parameter value for one of the first set or second set of input parameters $p_t$ and calculates a new current dose rate $d_t$ based on the new input parameter value.

9. The system according to claim 8, wherein the multiplication factor $f_i(w_i,p_t)$ is based on a path length by which a simulated x-ray beam would have traveled through the one or more simulated anatomies, the multiplication factor $f_i(w_i,p_t)$ determined utilizing a reference path length $l_{ref}$ and a path length $l_t$ at time point t.

10. The system according to claim 8, wherein the multiplication factor $f_i(w_i,p_t)$ is based on a fluoroscopic pulse rate, the multiplication factor $f_i(w_i,p_t)$ determined utilizing a reference pulse rate $p_{ref}$ and a pulse rate $p_t$ at time point t.

11. The system according to claim 8, wherein the multiplication factor $f_i(w_i,p_t)$ is based on a fluoroscopic dose level, wherein the multiplication factor $f_i(w_i,p_t)$ is inversely proportional to weight $w_i$ when the fluoroscopic dose level is in a low mode, the multiplication factor $f_i(w_i,p_t)$ is equal to 1 when the fluoroscopic dose level is in a normal mode, and the multiplication factor $f_i(w_i,p_t)$ is equal to weight $w_i$ when the fluoroscopic dose level is in a high mode.

12. The system according to claim 8, wherein the multiplication factor $f_i(w_i,p_t)$ is based on cine acquisition of the x-ray equipment model, wherein the multiplication factor $f_i(w_i,p_t)$ is equal to 1 when the cine acquisition is off, and the multiplication factor $f_i(w_i,p_t)$ is equal to weight $w_i$ when the cine acquisition is on.

13. The system according to claim 8, wherein the multiplication factor $f_i(w_i,p_t)$ is based on a cine acquisition frame rate of the x-ray equipment model, the multiplication factor $f_i(w_i,p_t)$ determined utilizing a reference cine frame rate $p_{ref}$ and a cine frame rate $p_t$ at time point t.

14. The system according to claim 8, wherein the multiplication factor $f_i(w_i,p_t)$ is based on a source image distance, the multiplication factor $f_i(w_i,p_t)$ determined utilizing a reference source image distance $s_{ref}$ and a source image distance $s_t$ at time point t.

15. The system according to claim 8, wherein the multiplication factor $f_i(w_i,p_t)$ is based on collimation of the x-ray equipment model, the multiplication factor $f_i(w_i,p_t)$ determined utilizing a reference non-collimated area $a_{ref}$ and a non-collimated area $a_t$ at time point t.

16. The system according to claim 8, wherein the multiplication factor $f_i(w_i,p_t)$ is based on wedge filter usage of the x-ray equipment model, the multiplication factor $f_i(w_i,p_t)$ determined utilizing a non-collimated area $a_t^{coll}$ at time point t, and a non-collimated and a filtered area $a_t^{filter}$ at time point t.

17. The system according to claim 8, wherein the multiplication factor $f_i(w_i,p_t)$ is based on magnification levels of the x-ray equipment model, the multiplication factor $f_i(w_i,p_t)$ determined utilizing a reference field-of-view $v_{ref}$ and a field-of-view $v_t$ at time point t.

18. The system according to claim 8, wherein the multiplication factor $f_i(w_i,p_t)$ is based on digital subtraction angiography usage of the x-ray equipment model, wherein the multiplication factor $f_i(w_i,p_t)$ is equal to 1 when the digital subtraction angiography is off, and the multiplication factor $f_i(w_i,p_t)$ is equal to weight $w_i$ when the digital subtraction angiography is on.

19. A system for simulating an x-ray guided medical procedure on a human and determining an amount of radiation exposure to one or more humans during the x-ray guided medical procedure, the system comprising:

an x-ray equipment model that simulates emission of radiation from x-ray equipment during the x-ray guided medical procedure, the x-ray equipment model comprising x-ray equipment input parameters corresponding to operating settings controlled during the x-ray guided medical procedure, wherein the x-ray equipment input parameters are configured to vary during the x-ray guided medical procedure;

a human exposure model for simulating the structure of one or more human anatomies during the x-ray guided medical procedure, the human exposure model comprising human exposure input parameters;

a radiation metric processor for calculating radiation exposure metrics to one or more humans located in a room of the x-ray guided medical procedure based on the x-ray equipment model and the human exposure model, wherein, during the x-ray guided medical procedure, the radiation metric processor modifies the radiation exposure metrics in response to variations of the x-ray equipment input parameters and human exposure input parameters using a model that associates a change in the x-ray equipment input parameters and human exposure input parameters with a change in the radiation exposure metrics; and a data collection storage that stores the modified radiation metrics;

wherein the model that associates the change in the x-ray equipment input parameters and human exposure input parameters with the change in the radiation exposure metrics calculates a current dose rate $d_r$.

20. A method for determining an amount of radiation exposure to one or more humans during a simulated x-ray guided medical procedure without exposing a human to ionizing radiation, the method comprising the steps of:

simulating, with an x-ray equipment model, emission of radiation from x-ray equipment during the simulated x-ray guided medical procedure without emitting ionizing radiation, the x-ray equipment model comprising a first set of input parameters corresponding to operating settings controlled during the simulated x-ray guided medical procedure, wherein the first set of input parameters are configured to vary during the simulated x-ray guided medical procedure, and wherein the x-ray equipment model calculates a geometry of x-ray beams emitted from an x-ray source;

simulating, with a human exposure model, one or more human anatomies during the simulated x-ray guided medical procedure, the human exposure model comprising a second set of input parameters corresponding to a location and structure of one or more human anatomies during the simulated x-ray guided medical procedure, and wherein the human exposure model calculates a size and shape of one or more human anatomies;

calculating with a radiation metric processor, a radiation exposure metric to the one or more humans based on the size and shape of the one or more human anatomies and the geometry of the x-ray beam emission, wherein calculating a radiation exposure metric occurs during the simulated x-ray guided medical procedure and is based on the first set and second set of input parameters and a model that associates a change in the first set and second set of input parameters with a change in the radiation exposure metric:

outputting, with a feedback system, information based on the radiation exposure metric during the simulated x-ray guided medical procedure, wherein the model that associates the change in the first set and second set of input parameters with the change in the radiation exposure metric calculates a current dose rate $d_r$.

* * * * *